(12) United States Patent
Eastenson et al.

(10) Patent No.: US 9,375,519 B2
(45) Date of Patent: Jun. 28, 2016

(54) BIOERODABLE POLY(ETHERESTERAMIDES) AND MEDICAL ARTICLE USES

(71) Applicant: SurModics, Inc., Eden Prairie, MN (US)

(72) Inventors: Kyle Eastenson, Bloomington, MN (US); Aleksey V. Kurdyumov, Lino Lakes, MN (US); Darin DuMez, Minneapolis, MN (US); Klaus Wormuth, Cologne (DE); Nathan A. Lockwood, Minneapolis, MN (US)

(73) Assignee: SurModics, Inc., Eden Prairie, MN (US)

( * ) Notice: Subject to any disclaimer, the term of this patent is extended or adjusted under 35 U.S.C. 154(b) by 0 days.

(21) Appl. No.: 13/926,357

(22) Filed: Jun. 25, 2013

(65) Prior Publication Data

US 2013/0344126 A1    Dec. 26, 2013

Related U.S. Application Data

(60) Provisional application No. 61/664,038, filed on Jun. 25, 2012.

(51) Int. Cl.

| | |
|---|---|
| *A61L 31/10* | (2006.01) |
| *A61L 31/14* | (2006.01) |
| *A61L 31/16* | (2006.01) |
| *A61K 47/48* | (2006.01) |
| *C08G 69/40* | (2006.01) |
| *C08G 69/44* | (2006.01) |
| *C08L 77/06* | (2006.01) |
| *C08L 77/12* | (2006.01) |
| *A61L 27/18* | (2006.01) |
| *A61L 27/34* | (2006.01) |
| *A61L 27/52* | (2006.01) |
| *A61L 27/54* | (2006.01) |
| *A61L 27/58* | (2006.01) |
| *A61L 31/06* | (2006.01) |

(52) U.S. Cl.
CPC ............ *A61L 31/10* (2013.01); *A61K 47/48992* (2013.01); *A61L 27/18* (2013.01); *A61L 27/34* (2013.01); *A61L 27/52* (2013.01); *A61L 27/54* (2013.01); *A61L 27/58* (2013.01); *A61L 31/06* (2013.01); *A61L 31/145* (2013.01); *A61L 31/148* (2013.01); *A61L 31/16* (2013.01); *C08G 69/40* (2013.01); *C08G 69/44* (2013.01); *C08L 77/06* (2013.01); *C08L 77/12* (2013.01); *A61L 2400/06* (2013.01)

(58) Field of Classification Search
CPC ...... C08L 77/12; C08L 77/06; A61L 2400/06; A61L 27/52; A61L 27/54; A61L 27/58; A61L 31/145; A61L 31/148; A61L 31/16; A61K 47/48992; C08G 69/40
USPC .......................... 424/426; 528/290; 514/772.3
See application file for complete search history.

(56) References Cited

U.S. PATENT DOCUMENTS

| | | | |
|---|---|---|---|
| 3,493,652 A | 2/1970 | Hartman | |
| 3,867,520 A | 2/1975 | Mori et al. | |
| 4,351,337 A | 9/1982 | Sidman | |
| 4,414,202 A | 11/1983 | Silvetti | |
| 4,778,679 A | 10/1988 | Silvetti | |
| 4,835,248 A | 5/1989 | Bader et al. | |
| 4,876,242 A | 10/1989 | Applebaum et al. | |
| 5,093,319 A | 3/1992 | Higham et al. | |
| 5,306,620 A | 4/1994 | Ginsberg et al. | |
| 5,380,656 A | 1/1995 | Barrett et al. | |
| 5,386,003 A | 1/1995 | Greene et al. | |
| 5,399,665 A | 3/1995 | Barrera et al. | |
| 5,468,480 A | 11/1995 | Barrett et al. | |
| 5,658,592 A | 8/1997 | Tanihara et al. | |
| 5,770,229 A | 6/1998 | Tanihara et al. | |
| 5,902,875 A | 5/1999 | Roby et al. | |
| 5,914,387 A | 6/1999 | Roby et al. | |
| 5,919,893 A | 7/1999 | Roby et al. | |
| 6,503,538 B1 | 1/2003 | Chu et al. | |
| 6,703,040 B2 * | 3/2004 | Katsarava et al. | 424/444 |
| RE40,359 E | 6/2008 | Katsarava et al. | |
| 8,030,436 B2 | 10/2011 | Pacetti et al. | |
| 2006/0188486 A1 * | 8/2006 | Carpenter et al. | 424/93.7 |
| 2007/0237803 A1 * | 10/2007 | Cheng et al. | 424/426 |
| 2011/0027379 A1 | 2/2011 | Chu et al. | |

FOREIGN PATENT DOCUMENTS

| | | | |
|---|---|---|---|
| EP | 0 447 719 | 9/1991 | |
| EP | 0 560 014 | 9/1993 | |
| EP | 0 712 635 | 5/1996 | |
| JP | 04-103566 | 4/1992 | |
| WO | WO 98/32398 | 7/1998 | |
| WO | WO 98/32777 | 7/1998 | |
| WO | WO 03/062298 | 7/2003 | |
| WO | WO03/062298 | * 7/2003 | C08G 63/00 |

(Continued)

OTHER PUBLICATIONS

Guo et al. (Biomacromolecules 2007, 8, 2851-2861).*
Biomedical Engineering Desk Reference (Classes of materials used in medicine; Chapter 3.2, pp. 215-217 2009).*
PCT Search Report for International Application No. PCT/US2013/047623 mailed on Oct. 25, 2013.
Arabuli, et al, "Heterochain Polymers Based on Natural Amino Acids. Synthesis and Enzymatic Hydrolysis of Regular Polyester Amides Based on Bis(L-phenylalanine) α,ω-Alkylene Diesters and Adipic Acid," Macromolecular Chemistry and Physics, vol. 195, Jun. 1994, pp. 2279-2289.
Castaldo, et al, "Synthesis and Preliminary Characterisation of Polyesteramides Containing Enzymatically Degradable Amide Bonds," Polymer Bulletin, vol. 28, No. 3, May 1992, pp. 301-307.

(Continued)

*Primary Examiner* — Anna Falkowitz
(74) *Attorney, Agent, or Firm* — Kagan Binder, PLLC

(57) ABSTRACT

Bioerodable poly(etheresteramides) and matrices formed therefrom, such as medical device coatings, are described. The matrices show desirable erosion properties desirable for therapeutic use. The matrices can include a bioactive agent which can be used to treat medical conditions.

18 Claims, 8 Drawing Sheets

(56) References Cited

FOREIGN PATENT DOCUMENTS

| WO | WO 2008/005438 | 10/2008 |
|---|---|---|
| WO | WO 2011/045443 | 4/2011 |

OTHER PUBLICATIONS

Fan, et al, "Synthesis and Specific Biodegradation of Novel Polyesteramides Containing Amino Acid Residues," Journal of Polymer Science, Polymer Chemistry Edition 39, No. 9, May 1, 2001, pp. 1318-1328.

Grigorieva, et al, "Biodegradable Polymers for Medical Applications," Advances in Plastics Technology, Conference Papers, 3rd, Katowice, Poland, Nov. 16-18, 1999, Institute of Plastics and Paint Industry (Abstract only).

Grigorieva, et al., "Advances in Plastics Technology," Biodegradable Polymers for Medical Applications ,1999, (13 pgs).

Guo et al. "Synthesis, Characterization, and Biodegradation of Novel Poly(ether ester amide)s Based on L-Phenylalanine and Oligoethylene Glycol," Biomacromolecules, 2007, 8:2851-2861.

Katsarava, et al, "Wound Dressing (Phagoderm)", Patent Department, Republic of Georgia, Jul. 1997, pp. 1 and 2.

Katsarava, et al, "Amino Acid-Based Bioanalogous Polymers, Synthesis, and. Study of Regular Poly(ester amide)s Based on Bis(a-amino acid) a,ω-Alkylene Diesters, and Aliphatic Dicarboxylic Acids," Journal of Polymer Science: Part A: Polymer Chemistry, 37: 391-407 (1999).

Kharadze, et al, "Synthesis and α-Chymotrypsinolysis of Regular Polyester Amides Based on Phenylalanine, Diols, and Terephthalic Acid," Polymer Science, Series A, vol. 41, No. 9, Sep. 1999, pp. 883-890.

Kuroyanagi , et al, "A Silver-Sulfadiazine-Impregnated Synthetic Wound Dressing Composed of Poly-$_L$-Leucine Spongy Matrix: An Evaluation of Clinical Class," J. Appl. Biomateer., 3: 153-161 (1992).

Kuroyanagi, et al, Evaluation of a Synthetic Wound Dressing Capable of Releasing Silver Sulfadiazine, J. Burn Care Rehabil., 12: 106-115 (1991).

Paredes, et al, "Studies on the Biodegradation and Biocompatibility of a New Poly(ester amide) Derived from L-Alanine," Journal of Applied Polymer Science, vol. 69, No. 8, Aug. 22, 1998, pp. 1537-1549.

Rodriguez-Galan, et al, "Comparative Studies on the Degradability of Polyester Amides Derived from L- and L,D-Alanine," Journal of Applied Polymer Science, vol. 74, No. 9, Nov. 28, 1999, pp. 2312-2320.

Saotome, et al, "Novel Enzymatically Degradable Polymers Comprising α-Amino Acid, 1,2-Ethanediol, and Adipic Acid," Chemistry Letters 1991, 21-24.

Saotome, et al, "Enzymic Degrading Solubilization of a Polymer Comprising Glycine, Phenylalanine, 1,2-Ethanediol, and Adipic Acid," the Chemical Society of Japan, Chemistry Letters, (1), 1991, pp. 153-154.

Schwartz, J., "Science Looks to Engineers for Solutions to Medicine's Most Perplexing Problems," Cornell Engineering Magazine, pp. 5-10 (1997).

Soothill, et al, "The Efficacy of Phages in the prevention of the destruction of pig skin in vitro by *Pseudomonas aeruginosa*," Med. Sci. Res., 16: 1287-1288 (1988).

Tsitalanadze et al, "AminoAcid Based Bioanalogous Polymers. Some Biological Studies of Regular Poly(Ester Amide)s and Bioactive Composites Based on Them," International Symposium on Biodegradable Materials, p. 122, Hamburg, Germany (1996).

\* cited by examiner

Molecular Weight: 1035.24 t=0 t=90d

BIOERODABLE POLY(ETHERESTERAMIDES) AND MEDICAL ARTICLE USES

CROSS-REFERENCE TO RELATED APPLICATION

The present non-provisional Application claims the benefit of commonly owned provisional Application having Ser. No. 61/664,038, filed on Jun. 25, 2012, entitled BIOERODABLE POLY(ETHERESTERAMIDES) AND MEDICAL ARTICLE USES, which Application is incorporated herein by reference in its entirety.

TECHNICAL FIELD

The present invention relates to biodegradable coatings for implantable medical articles. The method also relates to methods for treating medical conditions by releasing a bioactive agent from the coatings to a subject.

BACKGROUND

Amino acid-based poly(esteramides) (PEAs) can be prepared be reacting amino acid modified diols with activated diacids. PEAs have been proposed for use with biomedical articles based on their desirable physical and mechanical properties. Many PEAs have been reported to be "biodegradable" based on in vitro studies, however, the degradability was only observed under degradation conditions that did not properly reflect in vivo conditions.

SUMMARY OF THE INVENTION

Generally, the present invention relates to bioerodable poly(etheresteramides) and medical uses thereof, such for preparing and using erodable matrices for implantable or insertable medical articles. Subject matter of the invention includes bioerodable poly(etheresteramides), monomers and compositions used for making the poly(etheresteramides), polymeric matrices made from the bioerodable poly(etheresteramides), and implantable medical articles.

The bioerodable poly(etheresteramides) have a unique chemistry as provided by a combination of at least three different monomers, one of which provides a poly(ether) repeating segment. The polymer, including the poly(ether), provides reduced hydrophobicity and was demonstrated to have desirable degradation properties according to in vitro and in vivo experimental studies.

In some embodiments, the matrix is in the form of a coating on the surface of a medical device. It was shown that compositions including bioerodable poly(etherester-amides) adhered well to the surface of medical articles to which they were applied, and formed coatings with properties desirable for use in the body. In vivo experimental studies demonstrated the coatings were degradable over a prolonged time period, and showed that at least 50% (w/v) of the bioerodable polymeric matrix is capable of eroding within 6 months in vivo following implantation. In addition to the desirable rates of degradation in vivo, adverse reactions in the tissue surrounding the implanted and degraded matrices were not observed. For example, neither the polymer nor any of its degradation byproducts caused long-term inflammatory response in the tissue.

In some aspects the invention provides a bioerodable polymer comprising units of Formula I:

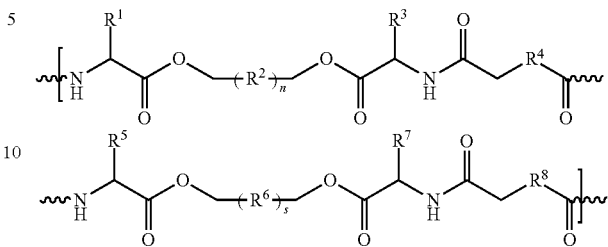

wherein $R^1$, $R^3$, $R^5$, and $R^7$ are independently selected from: —$CH(CH_3)_2$, —$CH_2CH(CH_3)_2$, —$CH(CH_3)CH_2CH_3$, —$(CH_2)_3CH_3$, —$CH_2C_6H_5$, —$(CH_2)_2SCH_3$, —$CH_3$, —$CH_2SH$, —$CH_2CO_2H$, —$(CH_2)_2CO_2H$, —H, —$CH_2$-imidazole, —$(CH_2)_4NH_2$, —$CH_2CONH_2$, —$(CH_3)_3$—$N_\alpha$ (cyclic), —$(CH_2)_2CONH_2$, —$(CH_2)_3NHC(NH_2)_2^+$, —$CH_2OH$, —$CH(CH_3)OH$, —$CH_2$-indole, and —$CH_2$—$C_6H_4$—OH; $R^2$ and $R^6$ are independently selected from divalent alkane, alkene (hydrocarbylene), and alkoxy (oxyalkylene), wherein the alkoxy is selected from —$CH_2OCH_2$— or —$CH_2OCH_2CH_2$—, wherein $(R^2)_n$ is different than and has a higher hydrophilic-lipophilic ratio than $(R^6)_s$; n is 1 or greater; s is 1 or greater; and $R^4$ and $R^8$ are independently selected from divalent, linear or branched, saturated or unsaturated, C1-C12 fragments.

In some specific embodiments, $R^1$, $R^3$, $R^5$, and $R^7$ are —$CH_2C_6H_5$; $R^2$ is —$CH_2OCH_2$—; n is 3; $R^6$ is —$(CH_2)$—; s is 6; and $R^4$ and $R^8$ are —$(CH_2)_3$—.

In some aspects the invention provides a composition comprising at least the following monomers (a)-(c):

(Formula II)

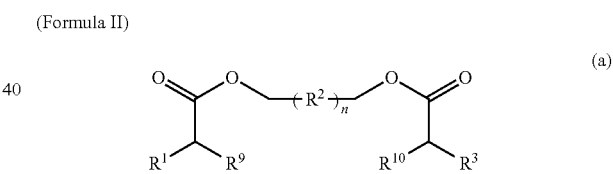

(a)

wherein $R^1$ and $R^3$ are independently selected from: —$CH(CH_3)_2$, —$CH_2CH(CH_3)_2$, —$CH(CH_3)CH_2CH_3$, —$(CH_2)_3CH_3$, —$CH_2C_6H_5$, —$(CH_2)_2SCH_3$, —$CH_3$, —$CH_2SH$, —$CH_2CO_2H$, —$(CH_2)_2CO_2H$, —H, —$CH_2$-imidazole, —$(CH_2)_4NH_2$, —$CH_2CONH_2$, —$(CH_3)_3$—$N_\alpha$ (cyclic), —$(CH_2)_2CONH_2$, —$(CH_2)_3NHC(NH_2)_2^+$, —$CH_2OH$, —$CH(CH_3)OH$, —$CH_2$-indole, and —$CH_2$—$C_6H_4$—OH; $R^2$ is selected from divalent alkane, alkene (hydrocarbylene), and alkoxy (oxyalkylene), wherein the alkoxy is selected from —$CH_2OCH_2$— or —$CH_2OCH_2CH_2$—; n is 1 or greater; and $R^9$ and $R^{10}$ are independently selected from: —$NH_2$ and —$NH_3^+X^-$, wherein X is a monovalent atomic or molecular cation;

(Formula III)

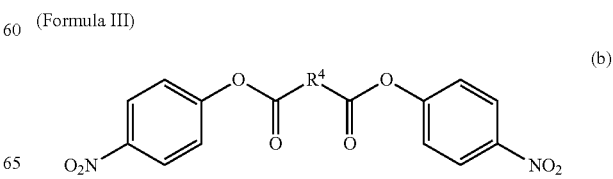

(b)

wherein R⁴ is a divalent, linear or branched, saturated or unsaturated, C1-C12 fragment; and (Formula IV)

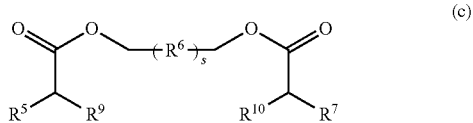

(c)

wherein R⁵ and R⁷ are independently selected from: —CH (CH₃)₂, —CH₂CH(CH₃)₂, —CH(CH₃)CH₂CH₃, —(CH₂)₃CH₃, —CH₂C₆H₅, —(CH₂)₂SCH₃, —CH₃, —CH₂SH, —CH₂CO₂H, —(CH₂)₂CO₂H, —H, —CH₂-imidazole, —(CH₂)₄NH₂, —CH₂CONH₂, —(CH₃)₃—N₊ (cyclic), —(CH₂)₂CONH₂, —(CH₂)₃NHC(NH₂)₂⁺, —CH₂OH, —CH(CH₃)OH, —CH₂-indole, and —CH₂—C₆H₄—OH; R⁶ is selected from divalent alkane, alkene (hydrocarbylene), and alkoxy (oxyalkylene), wherein the alkoxy is selected from —CH₂OCH₂— or —CH₂OCH₂CH₂—; s is 1 or greater; and R⁹ and R¹⁰ are independently selected from: —NH₂ and —NH₃⁺X⁻, wherein X is a monovalent atomic or molecular cation; and; where, in the composition, (R²)ₙ of monomer (a) has a higher hydrophilic-lipophilic ratio than (R⁶)ₛ of monomer (c).

Monomers of the composition, such as monomers (a)-(c) can be polymerized to form a bioerodable poly(etheresteramide) of the invention.

Other aspects of the invention provide a bioerodable polymeric matrix comprising the bioerodable poly(etheresteramide), and implantable or injectable biomedical articles comprising the bioerodable polymeric matrix. The matrix can be used on or in the body in various forms. For example, the matrix can be in the form of a coating on an implantable or insertable medical device, in the form of an adhesive layer between two portions of a medical implant, as a mass of polymeric matrix material in the body, or as a thin film applied to dermal tissue.

In some cases the polymeric matrix includes one or more bioactive agent(s). Accordingly, the invention also provides methods for delivering a bioactive agent to a subject comprising implanting, inserting, or injecting the biomedical article into a subject and allowing the bioactive agent to be released from the bioerodable polymeric matrix. In some modes of delivery, 50% (w/v) of the bioerodable polymeric matrix is capable of eroding within 6 months in vivo following implantation in a subject.

DETAILED DESCRIPTION

Figure 1:
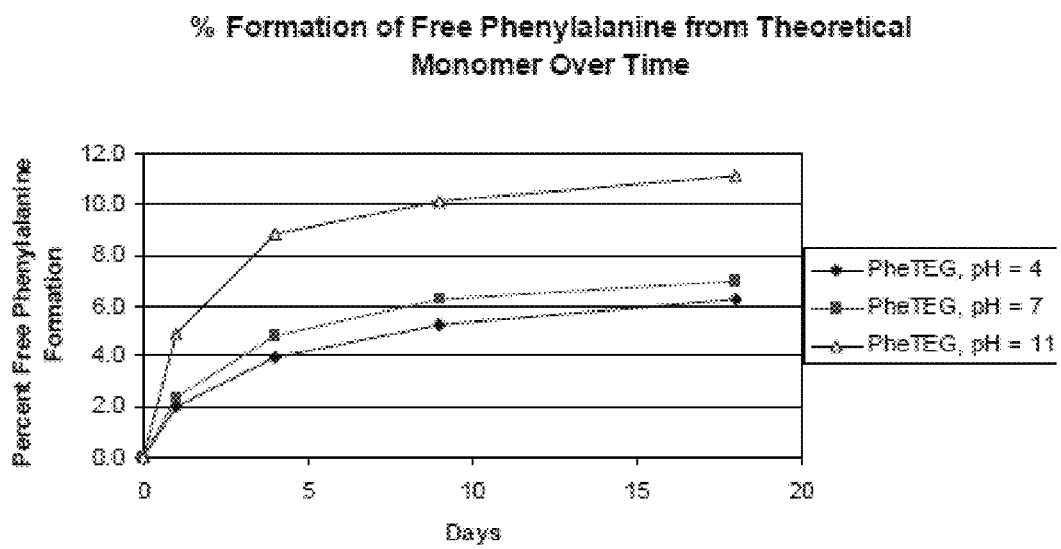
FIG. 1 is a graph showing degradation of the monomer Phe-TEG in aqueous solutions.

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The invention is generally directed to bioerodable poly (etheresteramides), matrices formed from these polymers, implantable or injectable biomedical articles comprising the bioerodable polymeric matrix, and monomers and compositions for making the polymers.

In exemplary modes of practice, bioerodable poly(etheresteramides) are formed from activated diacid and polyol (e.g., diol) monomer derivatives. Exemplary monomers for bioerodable poly(etheresteramides) synthesis were prepared and purified (Table 1). One monomer group is p-nitrophenol activated diacids according to monomer (b) (Formula III):

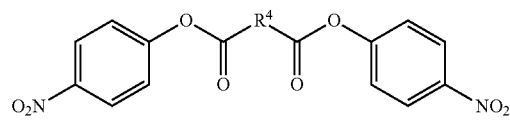

in which R⁴ is a divalent, linear or branched, saturated or unsaturated, C1-C12 fragment (hydrocarbylene). In some cases R⁴ is a divalent, linear or branched, saturated or unsaturated, C4-C8 fragment. Exemplary R⁴ groups include —CH₂—, —(CH₂)₂—, —(CH₂)₃—, —(CH₂)₄—, —(CH₂)₅—, —(CH₂)₆—, —(CH₂)₇—, —(CH₂)₈—, —(CH₂)₉—, —(CH₂)₁₀—, —(CH₂)₁₁—, —(CH₂)₁₂—,

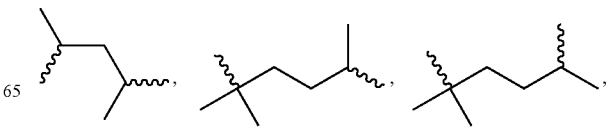

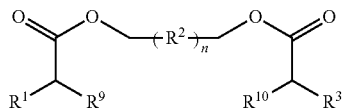

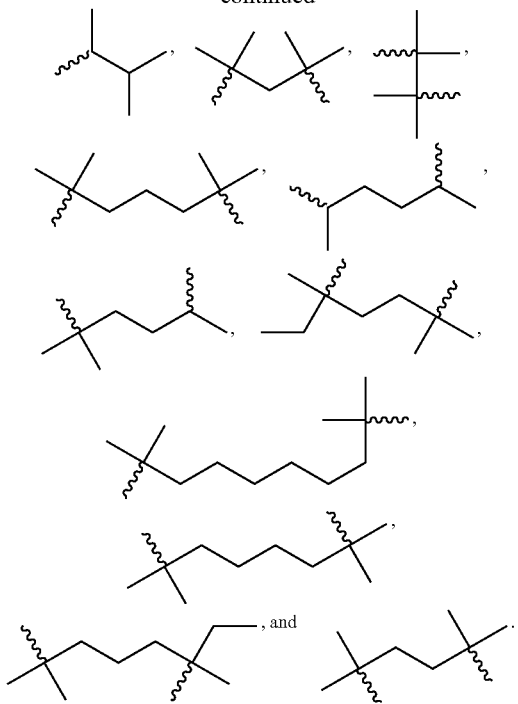

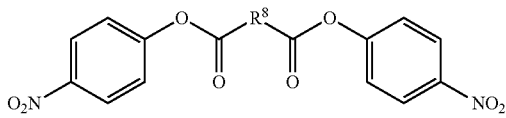

Exemplary dicarboxylic acids that can be used for making an activated diacid include, but are not limited to, malonic acid (propanedioic acid), succinic acid (butanedioic acid), glutaric acid (pentanedioic acid), adipic acid (hexanedioic acid), suberic acid (octanedioic acid), azelaic acid (nonanediaoic acid), sebacic acid (decanedioic acid), 2,4-dimethylglutaric acid, 2,5,5-trimethyladipic acid, 2,2,4,4-dimethylglutaric acid, 2,2,5-trimethyladipic acid, 2,3-dimethylsuccinic acid, 2,2,3,3-tetramethylsuccinic acid, 2,2,6,6-tetra-methylpimelic acid, 2,5-dimethyladipic acid, 2,2,5-trimethyladipic acid, 2,2,5-trimethyl-5-ethyladipic acid, 2,9-dibutylsebacic acid, 2,2,9,9-tetramethylsebacic acid, 2,2,7,7-tetramethylsuberic acid, 2,2,6-trimethyl-6-ethylpimelic acid and 2,2,5,5-tetramethyladipic acid, and the like.

It is understood that in some embodiments, the poly(etherester-amide) of Formula I can be formed using a single type of activated diacid (monomer (b); Formula III), and therefore, in these embodiments, $R^4$ and $R^8$ in Formula I are the same. In some embodiments the poly(etherester-amide) of Formula I can optionally be formed using two different activated diacids, such as with monomer (b) (Formula III), and also with monomer (d) (Formula V):

in which $R^8$ can be any group as described for $R^4$ with the proviso that $R^4$ and $R^8$ are different.

The para-nitrophenyl groups serve as leaving groups during monomer polymerization. Examples of (b) and (d) monomers (Formulas III and V) include "8" and "4" as shown in Table 1.

Other monomer groups are amino acid activated alkane- and alkene-based (hydrocarbylene), or alkoxy-based (oxyalkylene) diols according to monomer (a) (Formula II):

In (a), $R^1$ and $R^3$ can represent the side chain of any amino acid (e.g., $-CH(CH_3)_2$, $-CH_2CH(CH_3)_2$, $-CH(CH_3)CH_2CH_3$, $-(CH_2)_3CH_3$, $-CH_2C_6H_5$, $-(CH_2)_2SCH_3$, $-CH_3$, $-CH_2SH$, $-CH_2CO_2H$, $-(CH_2)_2CO_2H$, $-H$, $-CH_2$-imidazole, $-(CH_2)_4NH_2$, $-CH_2CONH_2$, $-(CH_3)_3-N_\alpha$ (cyclic), $-(CH_2)_2CONH_2$, $-(CH_2)_3NHC(NH_2)_2^+$, $-CH_2OH$, $-CH(CH3)OH$, $-CH_2$-indole, and $-CH_2-C_6H_4-OH$). $R^9$ and $R^{10}$ are, independently, primary amine groups or salts thereof (e.g., $-RH_2$ and $-RH_3^+$ $X^-$, wherein X is a monovalent atomic or molecular cation). $R^9$ and $R^{10}$ are reactive with the p-nitrophenol activated diacids according to monomer (b) (Formula III) and (d) (Formula V).

Also, $R^2$ is selected from divalent alkane, alkene (hydrocarbylene), and alkoxy (oxyalkylene), wherein the alkoxy is selected from $-CH_2OCH_2-$ and $-CH_2OCH_2CH_2-$; n is 1 or greater, in the range of 2 to 150, in the range of 2 to 50, in the range of 2 to 25, or in the range of 2 to 6. In the monomer (a), $(R^2)_n$ is different than and has a higher hydrophilic-lipophilic ratio than $(R^6)_s$ of monomer (c) (Formula IV). For example, the chemical group defining $(R^2)_n$ can provide monomer (a) with higher water solubility than monomer (c). As another example, the $(R^2)_n$ group has atoms selected from carbon, hydrogen, and one or more heteroatoms (such as O, N, and/or S). As another example, the $(R^2)_n$ group has atoms selected from carbon, hydrogen, and one or more heteroatoms (such as O, N, and/or S), and the $(R^6)$ of monomer (c) has a heteroatom or heteroatoms, as well, and the ratio of heteroatoms to carbon and hydrogen (e.g. (O, N, and/or S):(C and H)) in the $(R^2)_n$ group is greater than the ratio of heteroatoms to carbon and hydrogen (e.g. (O, N, and/or S):(C and H)) in the $(R^6)_s$ group.

Exemplary monomers (a) of formula II can be made by reacting a polyol (e.g., a diol), such as an ethylene glycol or propylene glycol, or poly(ethylene glycol) or poly(propylene glycol), with an amino acid-containing compound.

Representative examples of polyols include polyalkoxyalkanes such as poly(ethylene glycol), tetraethylene glycol, and triethylene glycol, trimethylolpropane ethoxylate, and pentaerythritol etholxylate. In many embodiments, the hydroxyl-containing compound used to make the monomer is an ethylene glycol polymer or oligomer having the structure $HO-(CH_2-CH_2-O)_n-H$. Typically, the value of n ranges from about 2 to about 150 and the number average molecular weight (Mn) of the poly(ethylene glycol) ranges from about 100 Da to about 5000 Da, and more typically from about 200 Da to about 3500 Da.

Other diols that can be used for the preparation of monomers of formula (a) include poloxamers. Poloxamers include a central hydrophobic poly(propylene oxide) portion with flanking hydrophilic poly(ethylene oxide) portions. Poloxamers, many of which are commercially available under the trade name Pluronics™ (BASF Corp.) include nonionic triblock copolymers of PEO-PPO-PEO having variations in the PPO core and the PEO content.

Examples of monomers of formula (a) include "Phe-TEG" and "Phe-PEG" as shown in Table 1. In some embodiments, the chemical group defining $(R^2)_n$ can provide monomer (a) with higher solubility in an organic solvent than monomer (c).

Other monomer groups are amino acid activated alkane-, alkene-, or alkoxy-based diols used as monomer (c) (Formula IV):

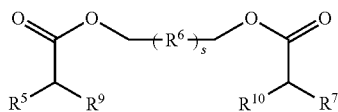

In (c), $R^5$ and $R^7$ can represent the side chain of any amino acid (e.g., —CH(CH$_3$)$_2$, —CH$_2$CH(CH$_3$)$_2$, —CH(CH$_3$)CH$_2$CH$_3$, —(CH$_2$)$_3$CH$_3$, —CH$_2$C$_6$H$_5$, —(CH$_2$)$_2$SCH$_3$, —CH$_3$, —CH$_2$SH, —CH$_2$CO$_2$H, —(CH$_2$)$_2$CO$_2$H, —H, —CH$_2$-imidazole, —(CH$_2$)$_4$NH$_2$, —CH$_2$CONH$_2$, —(CH$_3$)$_3$—N$_\alpha$ (cyclic), —(CH$_2$)$_2$CONH$_2$, —(CH$_2$)$_3$NHC(NH$_2$)$_2$$^+$, —CH$_2$OH, —CH(CH3)OH, —CH$_2$-indole, and —CH$_2$—C$_6$H$_4$—OH). $R^6$ is selected from divalent alkane, alkene (hydrocarbylene), and alkoxy (oxyalkylene), wherein the alkoxy is selected from —CH$_2$OCH$_2$— or —CH$_2$OCH$_2$CH$_2$—; and s is 1 or greater, where in monomer (c), $(R^6)_s$ is different than and has a lower hydrophilic-lipophilic ratio than $(R^2)_n$ of monomer (c) (Formula IV). $R^9$ and $R^{10}$ are, independently, primary amine groups or salts thereof (e.g., —RH$_2$ and —RH$_3$$^+$X$^-$, wherein X is a monovalent atomic or molecular cation). $R^9$ and $R^{10}$ can be reactive with the p-nitrophenol activated diacids according to monomer (b) (Formula III).

In some embodiments, the $(R^6)_s$ group has atoms selected from carbon and hydrogen, but does not include a heteroatom (such as O, N, and/or S). In some embodiments $R^6$ is a divalent, linear or branched, saturated or unsaturated, C1-C12 fragment (hydrocarbylene). In some cases $R^6$ is a divalent, linear or branched, saturated or unsaturated, C1-C8 fragment. Exemplary $R^6$ groups include —CH$_2$—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —(CH$_2$)$_{11}$—, —(CH$_2$)$_{12}$—,

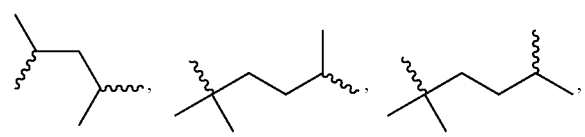

Exemplary monomers (c) of formula IV can be made by reacting an alkyl diol, such as one selected from the group consisting of butanediol, pentanediol, hexanediol, heptanediol, and octanediol, with an amino acid-containing compound.

In some embodiments, the chemical group defining $(R^6)_s$ can provide monomer (c) with higher solubility in an organic solvent than monomer (a).

Generally, materials and reaction conditions for the synthesis of exemplary monomers for the preparation of poly (etheresteramides) of the invention can be found in, for example, Guo et al (Biomacromolecules (2007) 8(9)2851-2861).

TABLE 1

| Name | Type | Structure |
| --- | --- | --- |
| di-p-nitrophenol sebacate ("8") (decanedioic acid bis-(4-nitrophenyl)ester) | p-nitrophenol activated diacid | 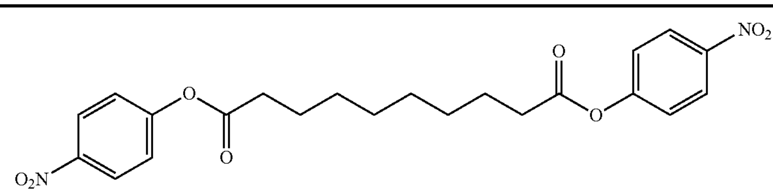 |
| di-nitrophenol-adipoyl ("4") (hexanedioic acid bis-(4-nitrophenyl)ester) | p-nitrophenol activated diacid | 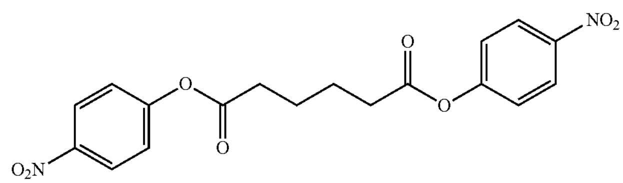 |

TABLE 1-continued

| Name | Type | Structure |
|---|---|---|
| "Phe-10" | amino acid activated alkyl-based diol | [structure: bis-(phenylalanine)-1,10-decylene diester · 2 pTsOH] |
| "Phe-4" di-p-toluenesulfonic salt of bis-(phenylalanine)-1,6-butylene diester | amino acid activated alkyl-based diol | [structure: bis-(phenylalanine)-1,4-butylene diester · 2 pTsOH] |
| L-phenylalanine-TEG ("Phe-TEG") (di-p-toluenesulfonic salt of bis-(phenylalanine)-tetraethylene glycol diester) | amino acid activated alkoxy-based diol | [structure: bis-(phenylalanine)-tetraethylene glycol diester · 2 pTsOH] |
| "Phe-PEG" | amino acid activated alkoxy-based diol | [structure: bis-(phenylalanine)-PEG diester · 2 pTsOH] |

Monomers of formula II were evaluated for degradation in water at basic, neutral, and acidic pH conditions. The Phe-TEG monomer showed evidence of degradation.

NMR indicated an increasing presence of free phenylalanine, a degradation byproduct, in solution over time (FIG. 1). The increase in Phe in solution was larger under basic conditions than neutral or acidic. This is consistent with hydrolysis of the ester bond in the Phe-TEG monomer.

Bioerodable poly(etheresteramides) of the invention can be formed by combining monomers (a), (b), and (c) at desired ratios and polymerizing the monomers to form the polymer. The molar ratio of monomers (a) to (c) can be chosen based on the chemical structure and properties of $(R^2)_n$ and $(R^6)_s$ respectively, so in the polymer product $(R^2)_n$ has a higher hydrophilic-lipophilic ratio than $(R^6)_s$. In embodiments of the invention, the polymer is prepared by an equimolar ratio of monomer (b) to monomers (a+c). In some aspects the composition comprises monomer (a) in a mole percentage range of about 1 to 49, monomer (b) in a mole percentage of about 50 and monomer (c) in a mole percentage range of about 1 to 49. The mole ratio of monomers (a) and (c) can be chosen based on properties of the monomers and the desired polymer property.

In some exemplary modes of synthesis, desired amounts of dry monomers (the amounts are based on desired mole ratios of monomer residues in the final polymer) are placed into an oven-dried round-bottom flask under inert atmosphere of nitrogen and equipped with a mechanical stirrer. Next, dry dimethylacetamide and triethylamine are added and the heterogeneous mixture is carefully stirred and heated at a temperature of about 80° C. After the reactants melt, stirring speed is slightly increased and the reaction mixture is allowed to stir at 80° C. After 6 days the reaction mixture is poured into DI water resulting in a rubbery precipitate which is then collected. Polymers are purified by extensively washing with saturated aqueous $NaHCO_3$ and water. Residual p-nitrophenol is removed by dissolving the polymer in chloroform and extracting with water until aqueous layer is colorless. An alternative purification procedure can involve triturating solid polymer in EtOAc with ~5% acetone for 3 days.

In some embodiments, exemplary bioerodable poly(etheresteramide) of the invention are water-insoluble materials. In many cases the polymers have an oil-like or waxy solid consistency. Polymer properties can be modulated by choosing desired chemical features of $(R^2)_n$, $(R^6)_s$, $R^4$, and $R^8$ in the polymer based on selection of monomers. See Table 2.

TABLE 2

| Polymer (monomer combination) | Description |
|---|---|
| "8" + "Phe-TEG" (8-Phe-TEG) | Light brown waxy solid |
| "4" + "Phe-TEG" (4-Phe-TEG) | Light brown waxy solid |
| "4" + "Phe-TEG" + "Phe-8" (4-Phe-TEG-Phe-8) | Light brown waxy solid |
| "4" + "Phe-PEG$_{2000}$" (4-Phe-PEG$_{2000}$) | Brown oil (at rt), soluble in water |
| "4" + "Phe-PEG$_{2000}$" + "Phe-4" (4-Phe-PEG$_{2000}$-Phe-4) | Light brown waxy solid, insoluble in water |

Polymerization of the monomers can provide a polymer including repeating units of Formula I:

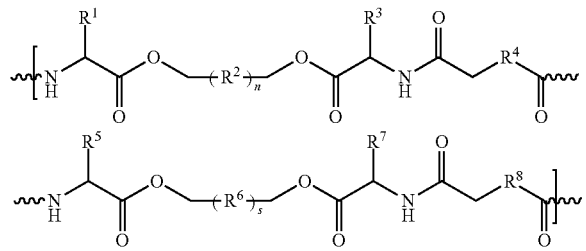

wherein $R^1$, $R^3$, $R^5$, and $R^7$ are independently selected from: —CH(CH$_3$)$_2$, —CH$_2$CH(CH$_3$)$_2$, —CH(CH$_3$)CH$_2$CH$_3$, —(CH$_2$)$_3$CH$_3$, —CH$_2$C$_6$H$_5$, —(CH$_2$)$_2$SCH$_3$, —CH$_3$, —CH$_2$SH, —CH$_2$CO$_2$H, —(CH$_2$)$_2$CO$_2$H, —H, —CH$_2$-imidazole, —(CH$_2$)$_4$NH$_2$, —CH$_2$CONH$_2$, —(CH$_3$)$_3$—N$_+$ (cyclic), —(CH$_2$)$_2$CONH$_2$, —(CH$_2$)$_3$NHC(NH$_2$)$_2{}^+$, —CH$_2$OH, —CH(CH$_3$)OH, —CH$_2$-indole, and —CH$_2$—C$_6$H$_4$—OH; $R^2$ and $R^6$ are independently selected from divalent alkane, alkene (hydrocarbylene), and alkoxy (oxyalkylene), wherein the alkoxy is selected from —CH$_2$OCH$_2$— or —CH$_2$OCH$_2$CH$_2$—, wherein $(R^2)_n$ is different than and has a higher hydrophilic-lipophilic ratio than $(R^6)_s$; n is 1 or greater; s is 1 or greater; and $R^4$ and $R^8$ are independently selected from divalent, linear or branched, saturated or unsaturated, C1-C12 fragment. $R^4$ and $R^8$ can be the same or different.

The polymer of the invention wherein $(R^2)_n$ is different than and has a higher hydrophilic-lipophilic ratio than $(R^6)_s$ can be understood based on various embodiments within the scope of the invention. For example, the chemical group defining $(R^2)_n$ can be more hydrophilic than the chemical group defining $(R^6)_s$ (e.g., a compound defining the $(R^2)_n$ group can be more water soluble than a compound defining the $(R^6)_s$ group). As another example, the chemical group defining $(R^6)_s$ can be more hydrophobic than the chemical group defining $(R^2)_n$ (e.g., a compound defining the $(R^6)_s$ group can be more soluble in an organic solvent than a chemical group a compound defining the $(R^2)_n$ group).

The $(R^2)_n$ and $(R^6)_s$ groups can optionally be defined with regards to atom content. For example, in some embodiments, the $(R^6)_s$ group has atoms selected from carbon and hydrogen (i.e, no heteroatoms), and the $(R^2)_n$ group has atoms selected from carbon, hydrogen, and one or more heteroatoms (such as O, N, and/or S). In some embodiments, the $(R^6)_s$ group has atoms selected from carbon and hydrogen (i.e, no heteroatoms), and the $(R^2)_n$ group has atoms selected from carbon, hydrogen, and oxygen. In other embodiments, the $(R^2)_n$ group has atoms selected from carbon, hydrogen, and one or more heteroatoms (such as O, N, and/or S), and the $(R^6)_s$ group has atoms selected from carbon, hydrogen, and one or more heteroatoms (such as O, N, and/or S), and the ratio of heteroatoms to carbon and hydrogen (e.g. (O, N, and/or S):(C and H)) in the $(R^2)_n$ group is greater than the ratio of heteroatoms to carbon and hydrogen (e.g. (O, N, and/or S):(C and H)) in the $(R^6)_s$ group.

In some embodiments, $R^1$, $R^3$, $R^5$, and $R^7$ of Formula I are the same chemical group. In some embodiments, one or more of, or all of $R^1$, $R^3$, $R^5$, and $R^7$ of Formula I is —CH$_2$C$_6$H$_5$. In some embodiments, $R^1$ and $R^3$ are the same, and $R^5$ and $R^7$ are the same, but $R^1/R^3$ is different than $R^5/R^7$.

In some embodiments, $R^2$ is —CH$_2$OCH$_2$—. In some embodiments, n is in the range of 2 to 150, in the range of 2 to 50, in the range of 2 to 25, or in the range of 2 to 6. In some specific embodiments, $R^2$ is —CH$_2$OCH$_2$—; and n is 3.

In some embodiments, $(R^6)_s$ is a divalent, linear or branched, saturated or unsaturated, C1-C12 fragment. In some cases $(R^6)_s$ is a divalent, linear or branched, saturated or unsaturated, C1-C8 fragment. Exemplary $(R^6)_s$ groups include —CH$_2$—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —(CH$_2$)$_{11}$—, —(CH$_2$)$_{12}$—,

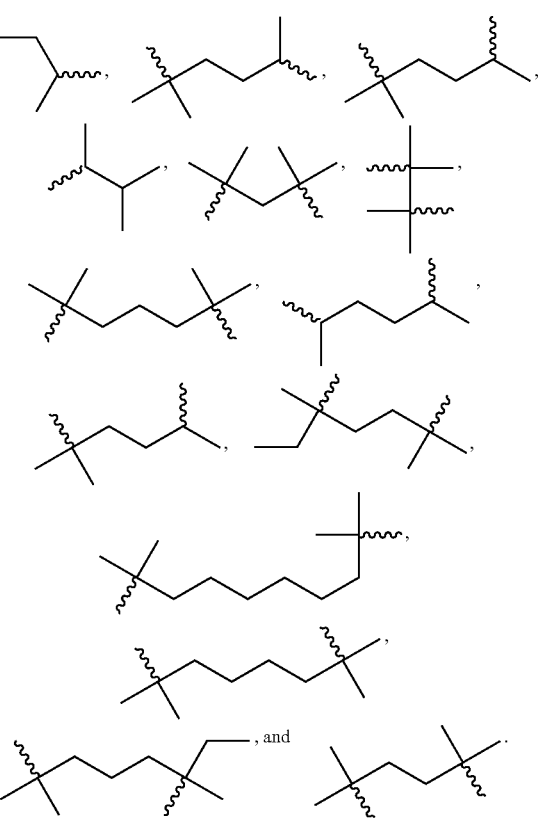

In some specific embodiments, $R^6$ is —(CH$_2$)— and s is 3.

In some aspects the bioerodable poly(etheresteramide) can be described in terms of molecular weight. The molecular weight of the polymer is more precisely defined as "weight average molecular weight" or $M_w$. $M_w$ is an absolute method of measuring molecular weight and is particularly useful for measuring the molecular weight of a polymer (preparation). Polymer preparations typically include polymers that individually have minor variations in molecular weight. Polymers are molecules that have a relatively high molecular weight and such minor variations within the polymer preparation do not affect the overall properties of the polymer preparation. The weight average molecular weight ($M_w$) can be defined by the following formula:

$$M_w = \frac{\sum_i N_i M_i^2}{\sum_i N_i M_i}$$

wherein N represents the number of moles of a polymer in the sample with a mass of M, and $\Sigma_i$ is the sum of all $N_i M_i$ (species) in a preparation. The $M_w$ can be measured using common techniques, such as light scattering or ultracentrifugation. Discussion of $M_w$ and other terms used to define the molecular weight of polymer preparations can be found in, for example, Allcock, H. R. and Lampe, F. W. (1990) *Contemporary Polymer Chemistry*; pg 271.

In some aspects, the poly(etheresteramide) is of [Formula I]$_n$, wherein n is an integer in the range of about 3 to about 100, or more specifically in the range of about 4 to about 50. Exemplary polymer molecular weights are in the range of about 3 kDa to about 100 kDa.

The mass of bioerodable poly(etheresteramide) material, in which bioactive agent can optionally be present can be described as a "polymeric matrix." In some cases, the matrix provides the structural framework for a coating. In many aspects, prior to erosion, the structural integrity of the coating can at least in part be based on the hydrophobic interactions in the matrix.

In some aspects the matrix is in the form of a coating on a medical article. A coating can be formed on all or a portion of the surface of an implantable medical article. In some aspects, bioactive agent can be included within the coating, and releasable from the coating following implantation of the article in a patient. In related aspects, the invention is also directed to methods for delivering bioactive agents to a subject from the coatings on the implantable medical articles.

The bioerodable poly(etheresteramide) can be present in one or more coated layers, on all or a portion of the surface of the implantable medical article. A "coating" as used herein can include one or more "coated layers", each coated layer including one or more coating materials. In some cases, the coating can be formed of a single layer of material that includes the bioerodable poly(etheresteramide). In other cases, the coating includes more than one coated layer, at least one of the coated layers including the bioerodable poly(etheresteramide). If more than one layer is present in the coating, the layers can be composed of the same or different materials.

If a bioactive agent is included in the coating it can be in the same coated layer as the bioerodable poly(etheresteramide), or in a different coated layer. The bioactive agent can be released from the coating following implantation in a subject. The bioactive agent can be released prior to degradation of the coating, prior to and during degradation of the coating, or during degradation of the coating. Alternatively, or additionally, the coated layer that includes the bioerodable poly(etheresteramide) can modulate bioactive agent release.

In some aspects, a bioerodable poly(etheresteramide) coating can be formed on a medical device. The device on which the bioerodable poly(etheresteramide) coating can be formed can be fabricated from various materials, including metals, plastics, other biomaterials, or combinations thereof. In some cases the implantable medical article is partially or entirely fabricated from a plastic polymer.

In some cases, the bioerodable poly(etheresteramide) coating can be formed on a medical device that is partially or entirely fabricated from a metal. Although many devices or articles are constructed from substantially all metal materials, such as alloys, some may be constructed from both non-metal and metal materials, where at least a portion of the surface of the device is metal. The metal surface may also be a thin surface layer. Such surfaces can be formed by any method including sputter coating metal onto all or portions of the surface of the device.

Metals that can be used in medical articles include platinum, gold, or tungsten, as well as other metals such as rhenium, palladium, rhodium, ruthenium, titanium, nickel, and alloys of these metals, such as stainless steel, titanium/nickel, nitinol alloys, cobalt chrome alloys, non-ferrous alloys, and platinum/iridium alloys. One exemplary alloy is MP35N. These metals, including other alloys or combinations, can be suitable substrates for disposing a coating composition containing the bioerodable poly(etheresteramide) of the invention.

The surface of metal-containing medical devices can optionally be pretreated (for example, with a Parylene™-containing coating composition) in order to alter the surface properties of the biomaterial, when desired. Metal surfaces can also be treated with silane reagents, such as hydroxy- or chloro-silanes.

The following list of medical articles is provided to illustrate surfaces on which the bioerodable poly(etheresteramide) can be applied to form a coating. These types of articles are typically introduced temporarily or permanently into a mammal for the prophylaxis or treatment of a medical condition. For example, these articles can be introduced subcutaneously, percutaneously or surgically to rest within an organ, tissue, or lumen of an organ, such as arteries, veins, ventricles, or atria of the heart.

Exemplary medical articles include vascular implants and grafts, grafts, surgical devices; synthetic prostheses; vascular prosthesis including endoprosthesis, stent-graft, and endovascular-stent combinations; small diameter grafts, abdominal aortic aneurysm grafts; wound dressings and wound management device; hemostatic barriers; mesh and hernia plugs; patches, including uterine bleeding patches, atrial septic defect (ASD) patches, patent foramen ovale (PFO) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parenteral feeding catheters, intravenous catheters (e.g., treated with antithrombotic agents), stroke therapy catheters, blood pressure and stent graft catheters; anastomosis devices and anastomotic closures; aneurysm exclusion devices; biosensors including glucose sensors; cardiac sensors; birth control devices; breast implants; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff, sewing cuff; spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; biliary drainage products.

In some aspects, a bioerodable poly(etheresteramide) coating is formed on a stent. Stents include vascular stents such as self-expanding stents and balloon expandable stents. "Expandable" means the stent can be expandable from a reduced diameter configuration utilizing an expansion member, such as a balloon. The particular configuration of the stent body is not critical to the invention described herein, and the inventive biodegradable materials and methods can be applied to virtually any stent configuration.

In some embodiments the stent is formed of a nonsolid material and provided with a bioerodable poly(etheresteramide) coating. The nonsolid material can include pores or other passages that can enable endothelial cells at the implantation site to grow into and over the stent so that biodegradation will occur within the vessel wall rather than in the lumen of the vessel.

In some aspects, the bioerodable poly(etheresteramide) matrix is in the form of a hydrogel. The hydrogel can be formed prior to implantation in a subject, or can be formed in situ, such as by injecting a matrix-forming composition that includes the bioerodable poly(etheresteramide) into a subject.

In yet other aspects, the bioerodable poly(etheresteramide) matrix is in the form of an adhesive. For example, the polymer adhesive can hold two portions of a medical implant together.

In yet other aspects, the bioerodable poly(etheresteramide) matrix is in the form of a freestanding film. A freestanding film can be a very thin (e.g., µm, mm, in thickness) patch made from the poly(etheresteramide) and optionally can include one or more bioactive agent(s), such as an anti-bacterial or antibiotic, or a bioactive agent to affect a certain dermal condition to be treated. The polymer film can have adhesive properties that permit application to a medical implant or a surface, such as biological surface like a dermal wound. For example, the film can be used to treat an ulcer (e.g., diabetic ulcers, pressure ulcers, stasis ulcers), burns (e.g., $1^{st}$ and $2^{nd}$ degree), abrasions; tissue injuries caused from chemical or electrical contact; decubitus (bed sores), frostbite, gangrene, psoriatic lesions; acne, carbuncles, erysipelas (dermal *streptococcus* infection), absesses, blisters; and pilonidal cysts.

The term "bioactive agent," refers to an inorganic or organic molecule, which can be synthetic or natural, which causes a biological effect when administered in vivo to a subject. The invention contemplates bioerodable poly(etheresteramide) matrices having bioactive agent within the matrix. The invention also contemplates coated medical articles wherein the bioactive agent is present in the article (such as within the body member of a biodegradable stent).

A partial list of bioactive agents is provided below. According to embodiments of the present invention, one may choose one or more of the bioactive agents to be included in a matrix formed of the bioerodable poly(etheresteramide) and/or coated medical article. A comprehensive listing of bioactive agents, in addition to information of the water solubility of the bioactive agents, can be found in *The Merck Index*, Thirteenth Edition, Merck & Co. (2001).

Bioerodable poly(etheresteramide) matrices prepared according to the invention can be used to release bioactive agents falling within one or more of the following classes include, but are not limited to: ACE inhibitors, actin inhibitors, analgesics, anesthetics, anti-hypertensives, anti polymerases, antisecretory agents, anti-AIDS substances, antibiotics, anti-cancer substances, anti-cholinergics, anti-coagulants, anti-convulsants, anti-depressants, anti-emetics, antifungals, anti-glaucoma solutes, antihistamines, antihypertensive agents, anti-inflammatory agents (such as NSAIDs), anti metabolites, antimitotics, antioxidizing agents, anti-parasite and/or anti-Parkinson substances, antiproliferatives (including antiangiogenesis agents), anti-protozoal solutes, anti-psychotic substances, anti-pyretics, antiseptics, anti-spasmodics, antiviral agents, calcium channel blockers, cell response modifiers, chelators, chemotherapeutic agents, dopamine agonists, extracellular matrix components, fibrinolytic agents, free radical scavengers, growth hormone antagonists, hypnotics, immunosuppressive agents, immunotoxins, inhibitors of surface glycoprotein receptors, microtubule inhibitors, miotics, muscle contractants, muscle relaxants, neurotoxins, neurotransmitters, polynucleotides and derivatives thereof, opioids, photodynamic therapy agents, prostaglandins, remodeling inhibitors, statins, steroids, thrombolytic agents, tranquilizers, vasodilators, and vasospasm inhibitors.

The bioactive agent can be an immunosuppressive agent, for example, rapamycin (sirolimus), ABT-578, cyclosporine, everolimus, mycophenolic acid, tacrolimus, and the like.

Examples of steroids include glucocorticoids such as cortisone, hydrocortisone, dexamethasone, betamethasone, prednisone, prednisolone, methylprednisolone, triamcinolone, beclomethasone, fludrocortisone, and aldosterone; sex steroids such as testosterone, dihydrotestosterone, estradiol, diethylstilbestrol, progesterone, and progestins.

A bioactive agent can be present in the coating in free (molecular) form, such as when, in preparing the coating, the bioerodable poly(etheresteramide) and the bioactive agent are soluble in a common coating solvent. Alternatively, the bioactive agent can be in particulate form, such as in the form of regular or irregularly-shaped nano- or microparticulates. A bioactive agent in particulate form may optionally not be soluble in the coating solvent, and therefore a coating with particulates contained within the matrix can be prepared.

The amount and type of bioactive agent may be chosen based on the type of the specific properties of the bioerodable poly(etheresteramide) used to form the coating, or the type and form of the bioactive agent present in the coating composition.

In some aspects, a bioactive agent can be released from the coated article during the entire in vivo lifetime, or during a portion of the coated article's in vivo lifetime. The bioactive agent can be present in the coating, within the structure of the article itself, or in both.

The period of time in which the bioactive agent is released from the coated article can be referred to as the "bioactive agent release period." If the bioactive agent release period is less than the in vivo lifetime of the coating, the bioactive agent is generally released from the coating at a rate faster than loss and/or degradation of the bioerodable poly(etheresteramide) from the coating. In this case, release of the bioactive agent out of the coating, such as by diffusion, may cause the bioactive agent release period to be less than the in vivo lifetime of the coating.

A "subject" refers to an organism in which the bioerodable poly(etheresteramide) matrix is placed and which the bioactive agent becomes available in following implantation. The subject can be a patient having a medical condition, wherein the condition is treatable using a bioactive agent that is released from the erodable matrices of the invention. The subject can be a human, another mammal, or a non-mammalian organism. For example, the subject can be a domesticated mammal such as a dog, cat, horse, cow, sheep, rabbit, etc. The subject can also be a bird, fish, or reptile.

In some cases a coating composition, such as one for a spray coating process, can be prepared having the bioerodable poly(etheresteramide) at a concentration in the range of about 5 mg/mL to about 100 mg/mL in the composition. In one mode of practice the bioerodable poly(etheresteramide) is present in the composition at about 40 mg/mL and the composition is used for coating a surface.

To illustrate one method of preparing a coating, a composition is prepared by combining a bioactive agent with a bioerodable poly(etheresteramide) in a solvent such as a halogenated alkane like methylene chloride or chloroform. The type of solvent system used can be chosen according to the bioerodable poly(etheresteramide), the bioactive agent, and any other optional component present in the composition.

Compositions of the invention that include the bioerodable poly(etheresteramide) in an organic solvent can be used to coat the surface of a variety of implantable medical devices. The coating composition (with or without bioactive agent) can be applied to a medical device using standard techniques to cover the entire surface of the device, or a portion of the device surface. If more than one coated layer is applied to a surface, it is typically applied successively. For example, a bioerodable poly(etheresteramide) coated layer can be formed by, for example, dipping, spraying, bushing, or swabbing the coating material on the article to form a layer, and then drying the coated layer. The process can be repeated to provide a coating having multiple coated layers, wherein at least one layer includes the bioerodable poly(etheresteramide). The compositions of the present invention are particularly suitable for use in spray coating processes.

An exemplary spray coating process and apparatus that can be used for coating implantable medical articles using the compositions of the present invention is described in U.S. Pat. No. 7,192,484 (Chappa et al.)

Other optional components can be included in the coating. These components can be included in amounts less than the amounts of bioerodable poly(etheresteramide) or bioactive agent in the coating. These optional components can change or improve the properties of the coating. Optional components can also be used to change the elasticity, flexibility, wettability, or adherent properties, (or combinations thereof) of the coating.

Optionally, components that can facilitate the detection of the implanted medical article can be used. These include colorants, radiopacifying agents, and radioisotopes, which can also be present in the coating. The presence of one or more of these components can facilitate detection of the location of article following implantation.

Implantable medical articles that include an erodible coating can be treated to sterilize one or more parts of the article, or the entire article. For example, a stent with an erodible coating can be sterilized before insertion into the body. In some aspects the coated article can be contacted with an aqueous sterilization solution.

According to some aspects of the invention, bioactive agent is made available to a subject using a method that involves the following steps. One step is implanting at a target site in a subject a medical article having a bioerodable coating comprising a matrix of bioerodable poly(etheresteramide) and bioactive-agent within the matrix. Another step is allowing the bioactive agent to be released from the coating in the subject following the step of implanting.

While the step of implanting can be performed to place the coated medical article at a desired location anywhere in the body, an exemplary process involves the placement of a stent having a bioerodable coating in the vasculature.

Stents with the bioerodable coating as described herein have particular application in the field of coronary angioplasty. As used herein, the terms "stent" and "prosthesis" are used interchangeably to some extent in describing the invention, insofar as the methods, apparatus, and structures of the invention can be utilized not only in connection with an expandable intraluminal vascular graft for expanding partially occluded segments of a vessel, duct, or body passageways, such as within an organ, but can also be utilized for many other purposes as an expandable prosthesis for many other types of body passageways. For example, expandable prostheses can also be used for such purposes as (1) supportive graft placement within blocked arteries opened by transluminal recanalization, but which are likely to collapse in the absence of internal support; (2) similar use following catheter passage through mediastinal and other veins occluded by inoperable cancers; (3) reinforcement of catheter created intrahepatic communications between portal and hepatic veins in patients suffering from portal hypertension; (4) supportive graft placement of narrowing of the esophagus, the intestine, the ureters, the urethra, and the like; (5) intraluminally bypassing a defect such as an aneurysm or blockage within a vessel or organ; and (6) supportive graft reinforcement of reopened and previously obstructed bile ducts. Accordingly, use of the term "prosthesis" encompasses the foregoing usages within various types of body passageways, and the use of the term "intraluminal graft" encompasses use for expanding the lumen of a body passageway. Further, the term "body passageway" encompasses any lumen or duct within the body, such as those previously described, as well as any vein, artery, or blood vessel within the vascular system.

Coated stents can be adapted for deployment and implantation using conventional methods known in the art and employing percutaneous transluminal catheter devices. Coated stents can be designed for deployment by any of a variety of in situ expansion means, such as an inflatable balloon or a polymeric plug that expands upon application of pressure. For example, the tubular body of the stent can be positioned to surround a portion of an inflatable balloon catheter. The stent, with the balloon catheter inside is configured at a first, collapsed diameter. The stent and the inflatable balloon are percutaneously introduced into a body lumen, following a previously positioned guidewire in an over-the-wire angioplasty catheter system, and tracked by suitable means (such as fluoroscopy) until the balloon portion and associated stent are positioned within the body passageway at the implantation site. Thereafter, the balloon is inflated and the stent is expanded by the balloon portion from the collapsed diameter to a second expanded diameter. After the stent has been expanded to the desired final expanded diameter, the balloon is deflated and the catheter is withdrawn, leaving the stent in place. During placement, the stent can optionally be covered by a removable sheath or other means to protect both the stent and the vessels.

For self-expanding stents, the following procedure can be applicable. In order to deliver a stent to the site of a stenotic lesion (implantation site), the external diameter of the stent is reduced so that the stent can easily traverse the blood vessels leading to the implantation site. The stent is disposed within the reduced diameter portion of the vessel. Thus, the stent is reduced by, for example, elongating the stent, allowing for a corresponding reduction in diameter, and maintained in such a reduced diameter or collapsed configuration during the delivery process. Once at the implantation site, the forces tending to reduce the diameter of the stent are released whereby the stent can support and/or dilate the stenotic portion of the vessel.

In some aspects, the stent can be delivered to an implantation site by placing the reduced diameter stent within a delivery sheath that is in turn fed through a guide catheter through the vasculature to the implantation site. The stent carrying sheath is then advanced from the distal end of the guide catheter over a guide wire into the targeted vessel and to the implantation site (site of a stenotic lesion).

A second sheath can be provided proximally of the collapsed stent and used to facilitate removal of the stent from the outer sheath. For example, once the sheath has been disposed at the implantation site of a vessel, the inner, proximal sheath is held in place while the outer sheath is retracted or pulled proximally with respect to the stent. Removal of the outer sheath removes the forces that retain the stent in its collapsed configuration and thus allow the stent to self-expand within the stenotic portion of the vessel to support and dilate the vessel walls. The inner sheath prevents the stent from moving proximally with the outer sheath. The inner and outer sheaths as well as the guide wire and guide catheter can then be removed from the vascular system. Alternatively, the inner and outer sheaths can be removed and a balloon catheter fed through the guide catheter over the guide wire and into the expanded stent. The balloon can then be inflated within the stent so as to urge the stent into firm engagement with the walls of the vessel and/or to augment the dilation of the artery effected by the stent alone.

In some aspects, the stent can be delivered to the implantation site on a balloon catheter. Such balloon catheters are well known and will not be described in more detail here.

Bioactive agent can be released for a period of time and in an amount sufficient to treat a medical condition in a subject, such as one suffering from a cardiovascular disease or compilation. Erosion of the bioerodable poly(etheresteramide) matrix can occur while the bioactive agent is being released from the coating, or can occur after bioactive agent is released.

The invention further contemplates use of bioerodable poly (etheresteramide) matrices, with or without bioactive agent, for treatment of medical conditions other than those in which intraluminal stenting is used.

Figure 2:
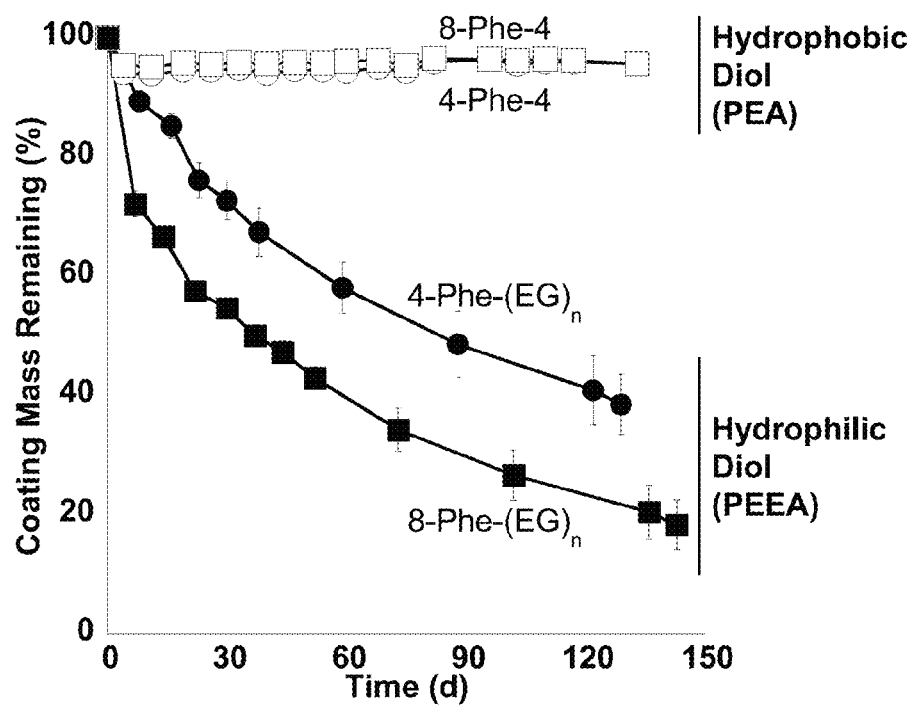
FIG. 2 is a graph of mass loss of PEEA and PEA coatings on parylene-treated stainless steel stents in PBS, pH 7.4, 37° C.
Figure 4:
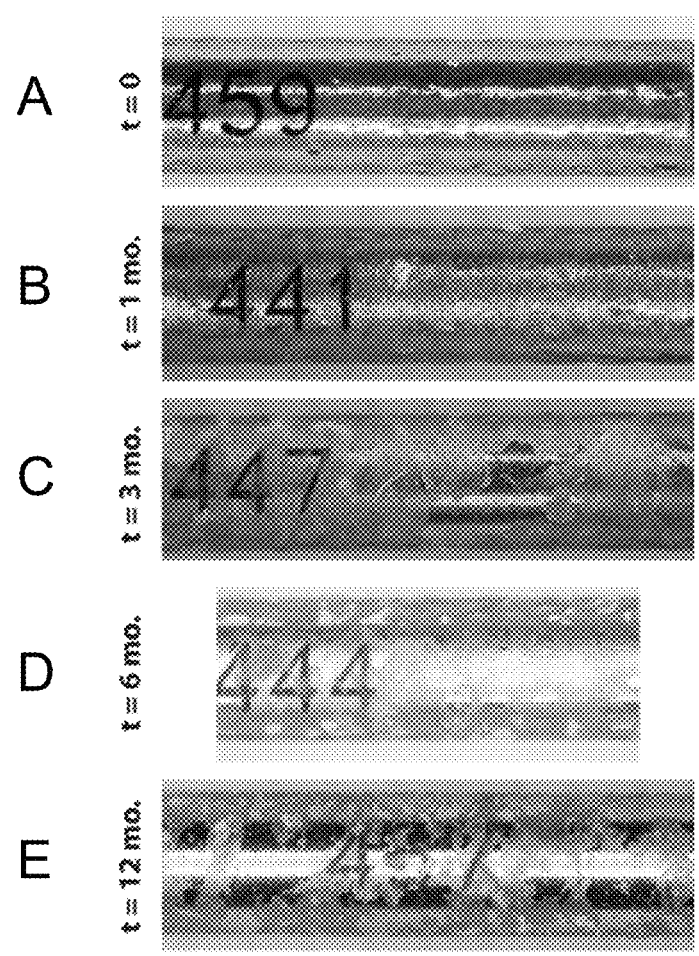
FIGS. 4A-E are micrographs of 4-Phe-TEG-8 coatings on stainless steel rods prior to implantation, and after 1, 3, 6, and 12 months of implantation in a subcutaneous model.

In vitro and in vivo studies carried out demonstrated mass loss of poly(etheresteramide)-based coatings over time. Stents coated with 8-Phe-TEG or 4-Phe-TEG and measured mass loss over time in PBS. Both polymers exhibited a loss of mass over roughly 4 months (FIG. 2). In in vivo studies, the amount of poly(etheresteramide)-based coatings visibly decreased during the course of the in vivo experiment (FIG. 4). The coating became thinner, more patchy, less brown, and more white over 12 months. Consistent with degradation studies in PBS, 4-Phe-TEG-8 coatings lost mass during the in vivo study (FIG. 5A).

Figure 10A:
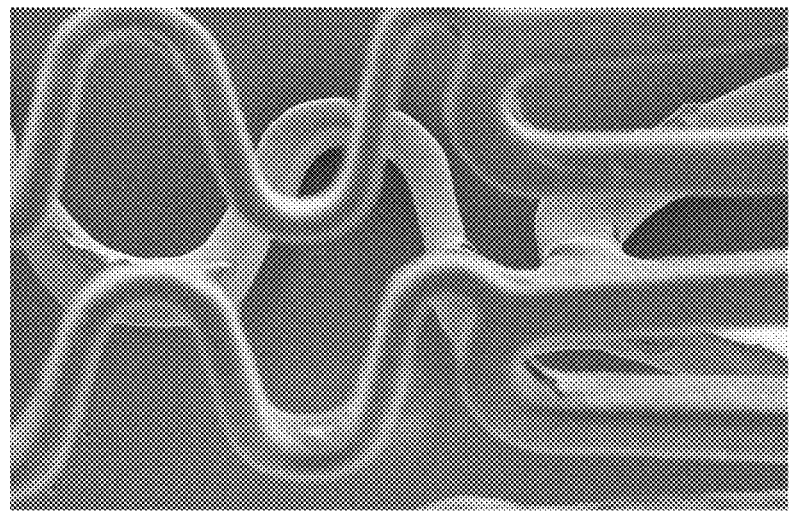
FIGS. 10A and B are micrographs of PEA coatings on stainless steel stents after periods of implantation in vivo.

Comparatively, stents coated with PEA polymers and incubated in vitro in PBS or serum showed little or no mass loss of polymer over roughly 6 months (FIG. 2). Likewise, stents coated with PEA polymers and implanted in vivo showed no clear change in the polymer coating over approximately 3 months (FIGS. 10A and B).

Analysis of the polymer was also carried out to understand the mechanism of degradation. Degradation of the poly (etheresteramide) polymers of the invention is expected to proceed by hydrolysis of esters in the backbone, leading to a decrease in the molecular weight of the polymer over time. The molecular weight of the poly(etheresteramide) polymers (4-Phe-TEG-8) polymer remaining in the coating decreased approximately 50% over the course of 12 months in vivo (FIG. 6), indicating the polymer is degrading and not simply dissolving over time.

Figure 7A:
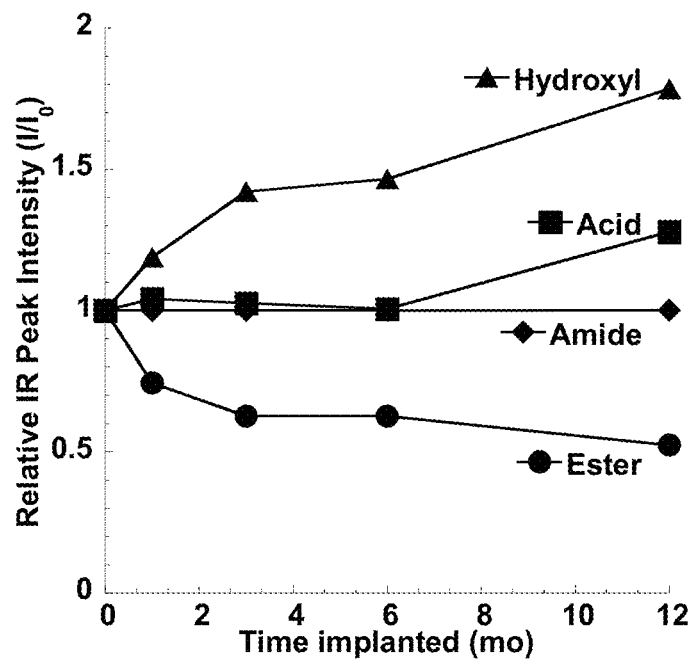
FIGS. 7A-B. (A) shows intensity of FTIR peaks corresponding to various carbonyls in 4-Phe-TEG-8 coatings after various times in vivo. (B) is a chemical structure illustration of PEEA degradation products.
Figure 7B:
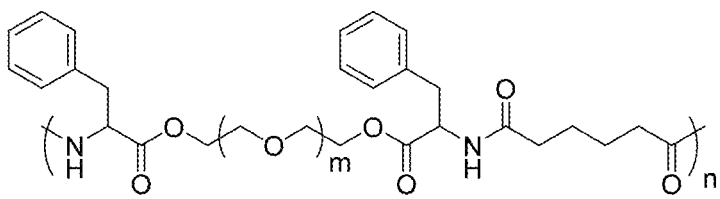
Figure 7B:
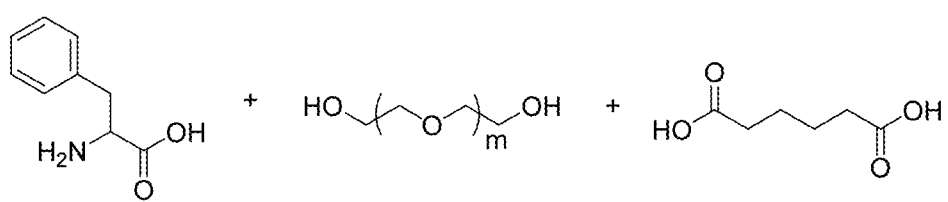

Infrared (IR) microscopy analysis of the coating remaining on the part of the coated stent at each endpoint was also carried out. The IR spectra changed systematically as residence time in vivo increased (FIG. 7). Peaks associated with the carbonyls of the polymer, which represents the location that hydrolysis is expected to occur, decreased over 12 months. A peak associated with a hydroxyl (OH) functionality increased with time and in a fashion that mirrored the decrease in the COOR peak, is thought to represent cleavage of the ester bond in the polymer back bone cleaved causing a decrease in COOR and an increase in OH at the cleavage site. As such, the data provides evidence that the esters in the backbone of the polymer hydrolyzed over time.

Figure 8A:
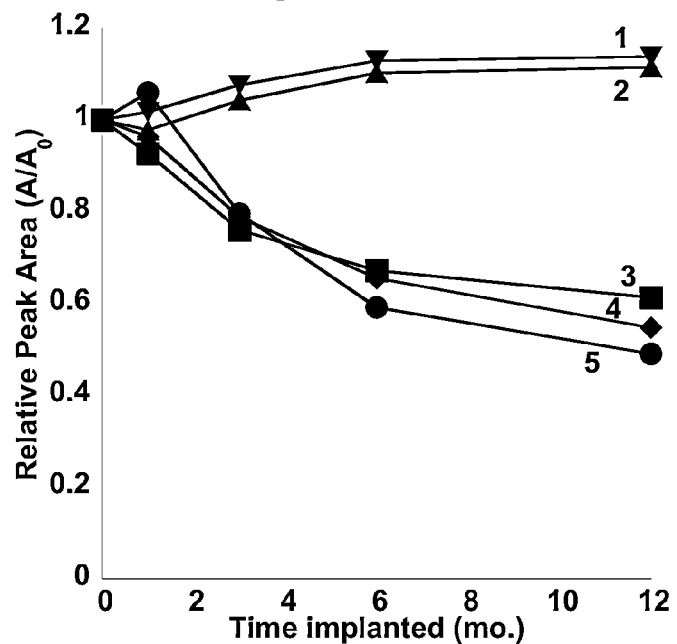
FIGS. 8A and B. (A) is graph of NMR peak intensity values of units of the 4-Phe-TEG-8 polymer as a function of residence time in vivo. Data points correspond to protons at sites noted by the same number on the schematic polymer structure in (B).
Figure 8B:
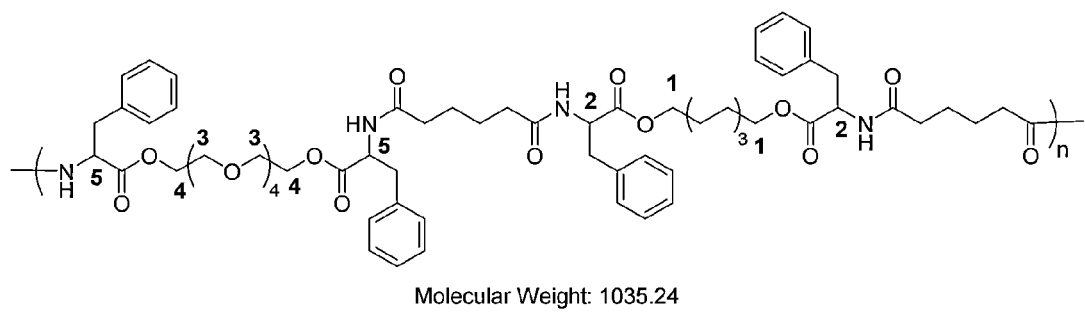

Nuclear magnetic resonance (NMR) analysis of the coating remaining on the part of the coated stent at each endpoint was also carried out. The NMR spectra changed systematically as residence time in vivo increased (FIG. 8). Peaks that were associated with the TEG repeat unit (positions 3 and 4 in FIG. 8) decreased over time, as did the peak assigned to the backbone Phe CH adjacent to the TEG repeats (position 2 in FIG. 8). Peaks associated with the Phe CH adjacent to the tetramethyl or octamethyl diol repeat and the outer $CH_2$s of these repeats increased slightly with time.

These results suggest that the 4-Phe-TEG-8 polymer preferentially loses TEG components relative to the other functional blocks. To complement this loss, there is a shift in the Phe CH proton signal (position Ha {δ4.91 ppm}/Hb {δ 4.85 ppm}) with a shift in signal intensity from Ha to more like Hb in chemical shift. The results can be explained by cleavage of the polymer at the ester between TEG and Phe. The NMR data is consistent with the interpretation of FTIR data discussed above.

There are no new signals in the proton spectrum to indicate the formation of other products as a result of this degradation process. This suggests that none of the degradation products (individual functional group fragments) remain with the recovered polymer.

Figure 9A:
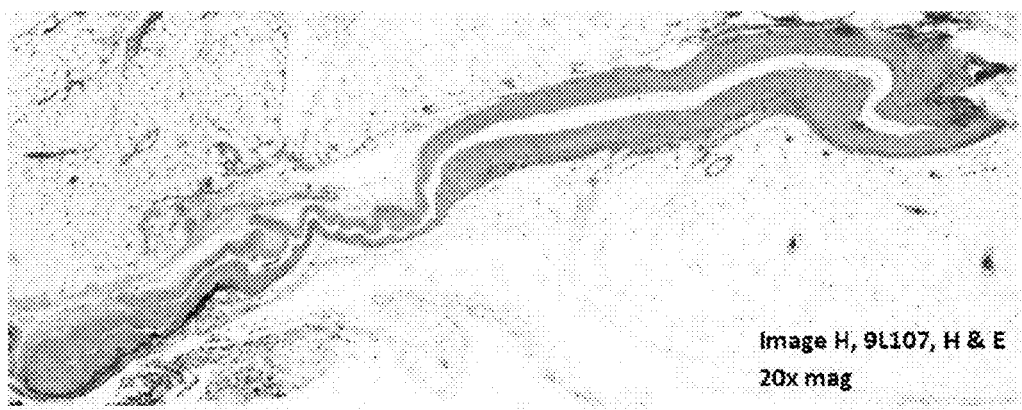
FIGS. 9A and B are micrograph images of tissue surrounding PEEA-coated implants.
Figure 9B:
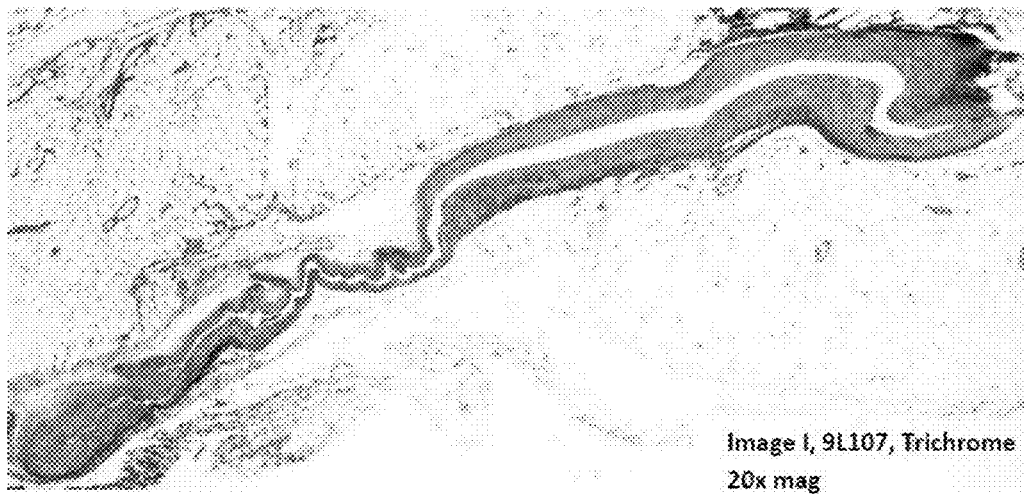

Rudimentary histology was performed on a small number of samples at the 12 month time endpoint of the in vivo study. The micrographs of FIG. 9 indicate that neither the polymer nor any of its degradation products caused any long-term inflammatory response in the tissue.

EXAMPLE 1

Preparation of Monomers: P-Nitrophenol Activated Diacids and Amino Acid Activated Alkoxy and Alkyl-Based Diols

TABLE 1

| Name | Type | Structure |
|---|---|---|
| di-p-nitrophenol sebacate ("8") (decanedioic acid bis-(4-nitrophenyl)ester) | p-nitrophenol activated diacid | 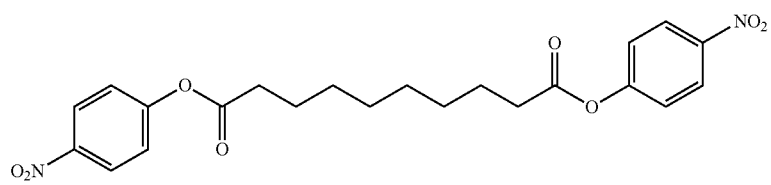 [SMILES: O=C(CCCCCCCCC(=O)Oc1ccc([N+](=O)[O-])cc1)Oc1ccc([N+](=O)[O-])cc1] |

TABLE 1-continued

| Name | Type | Structure |
|---|---|---|
| di-nitrophenol-adipoyl ("4") (hexanedioic acid bis-(4-nitrophenyl)ester) | p-nitrophenol activated diacid | 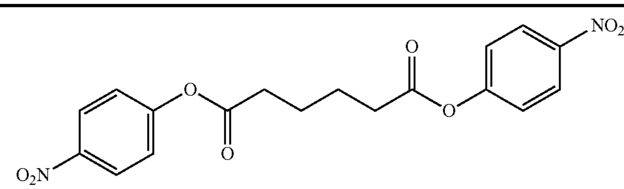 |
| "Phe-10" | amino acid activated alkyl-based diol | 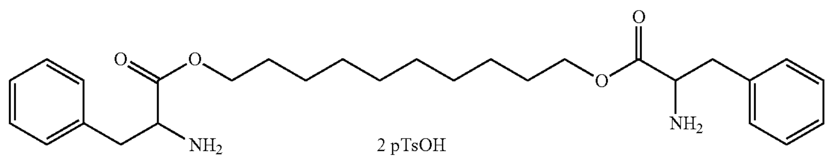 [SMILES: NC(Cc1ccccc1)C(=O)OCCCCCCCCCCOC(=O)C(N)Cc1ccccc1 ; "2 pTsOH"] |
| "Phe-4" di-p-toluenesulfonic salt of bis-(phenylalanine)-1,6-butylene diester | amino acid activated alkyl-based diol | 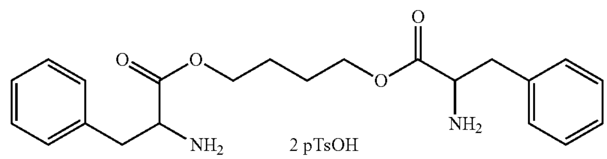 [SMILES: NC(Cc1ccccc1)C(=O)OCCCCOC(=O)C(N)Cc1ccccc1 ; "2 pTsOH"] |
| L-phenylalanine-TEG ("Phe-TEG") (di-p-toluenesulfonic salt of bis-(phenylalanine)-tetraethylene glycol diester) | amino acid activated alkoxy-based diol | 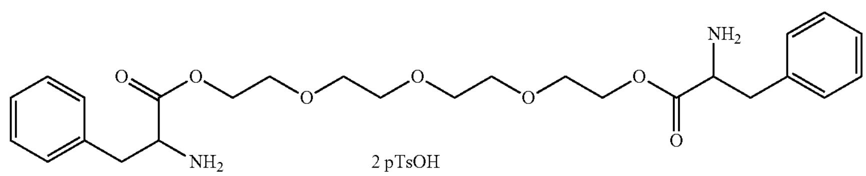 [SMILES: NC(Cc1ccccc1)C(=O)OCCOCCOCCOCCOC(=O)C(N)Cc1ccccc1 ; "2 pTsOH"] |
| "Phe-PEG" | amino acid activated alkoxy-based diol | 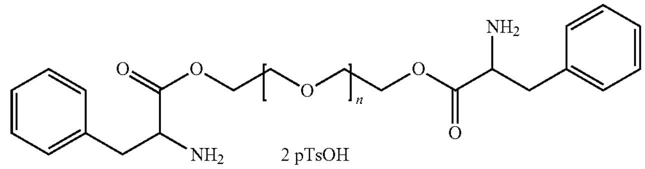 |

Phe-4 Synthesis

L-phenylalanine (33 g), 1,4-butanediol (8.64 g), p-toluenesulfonic acid (40 g) and toluene (250 mL) was placed in a 500 mL 3-neck round-bottom flask equipped with a Dean-Stark trap, temperature probe and a mechanical stirrer. The reaction mixture was brought to reflux while stirring. After 16 h, it was cooled to ambient temperature. The precipitate was collected by vacuum filtration and washed with toluene (3×50 mL). The crude product was dried under vacuum. The final product was purified by washing it extensively with DI water (1×250 mL, 5×50 mL) and acetone (3×30 mL). It was dried under vacuum. The structure was confirmed by $^1$H NMR analysis. Other diol derivatives (e.g., Phe-10, Phe-PEG, Phe-TEG) were made using the above procedure with slight modifications.

Di-p-Nitrophenol Adipoyl Synthesis p-Nirophenol (28.5 g) was dissolved in dry acetone (150 mL) in a dry 500 mL 3-neck round-bottom flask under inert atmosphere with stirring. The solution was cooled to 0-5° C. using external ice-water bath. Pyridine (16.6 mL) was slowly added followed by dropwise addition of adipoyl chloride (14.6 mL). The reaction temperature was kept under 6° C. by adjusting the adipoyl chloride addition. The reaction mixture was allowed to warm up to ambient temperature wile stirring for 2 h. At which point, it was cooled to 0-5° C., and the resulting white precipitate was collected by vacuum filtration. The crude product was washed with DI water (50 mL), 0.1N HCl (5×100 mL), DI water (5×100 mL) and ice-cold acetone (2×20 mL). The final product was purified by crystallization out of acetone. The structure was confirmed by $^1$H NMR analysis. Other acid derivatives (e.g., di-p-nitrophenol sebacate) were made using the above procedure with slight modifications.

EXAMPLE 2

Analysis of Monomer Degradation

Monomers were placed in deuterated water (adjusted to pH 4, 7, or 11 with DCl or NaOD) in an NMR tube and incubated at room temperature. NMR was used to detect the presence of free phenylalanine, a degradation byproduct, in the aqueous phase (see FIG. 1).

EXAMPLE 3

Preparation of PEA and PEEA Polymers (A) Preparation of 4-Phe-TEG-Phe-8
Desired amounts of dry monomers (di-p-nitrophenyl sebacate (11.25 mmol); di-p-toluenesulfonic salt of bis-(phenylalanine)-tetraethylene glycol diester (5.15 mmol); di-p-toluenesulfonic salt of bis-(phenylalanine)-1,6-butylene diester (7.72 mmol)) were placed into an oven-dried round-bottom flask which was under inert atmosphere of nitrogen and equipped with a mechanical stirrer. Dry dimethylacetamide and triethylamine were added and the heterogeneous mixture was stirred and heated at 80° C. After the reactants melted, stirring speed was slightly increased and the reaction mixture was allowed to stir at 80° C. After 6 days the reaction mixture was poured into DI water resulting in rubbery precipitate which was collected. The polymers were purified by extensively washing them with saturated aq. $NaHCO_3$ and water. The material was further purified by triturating the solid polymer in a non-dissolving solvent for 3 days. Other PEEAs were made using the above procedure with slight modifications.

TABLE 2

| Polymer (monomer combination) | Description |
| --- | --- |
| "8" + "Phe-TEG" (8-Phe-TEG) | Light brown waxy solid |
| "4" + "Phe-TEG" (4-Phe-TEG) | Light brown waxy solid |
| "4" + "Phe-TEG" + "Phe-8" (4-Phe-TEG-Phe-8) | Light brown waxy solid |
| "4" + "Phe-$PEG_{2000}$" (4-Phe-$PEG_{2000}$) | Brown oil (at rt), soluble in water |
| "4" + "Phe-$PEG_{2000}$" + "Phe-4" (4-Phe-$PEG_{2000}$-Phe-4) | Light brown waxy solid, insoluble in water |

EXAMPLE 4

Preparation of Coated Stents and Rods

Stents and stainless steel rods were coated with PEEA and PEA polymers and used for in vitro and in vivo coating degradation studies. As coating substrates, 3.0×13 or 3.0×18 mm stainless steel stents, and 3.0×20 mm 316 stainless steel rods were used. Rod samples had traceable ID numbers laser etched onto the surface.

Stent and rod coatings were carried out using a coating apparatus and process as described in U.S. Pat. No. 7,192,484 (Chappa et al.) Polymers were dissolved in chloroform (~40 mg/mL) and filtered before coating. All parts were dried under vacuum overnight after coating. Final coating weights were ~600 μg per stent and ~5 mg per rod.

EXAMPLE 5

Assessment of Mass Loss of PEA and PEEA-Coated Stents in PBS

Coated stents were placed in 1 mL PBS and incubated at 37° C. Degradation was assessed by removing stents, rinsing with water, drying, and weighing. PBS was refreshed at each measurement. The mass of PEA coatings did not change over >120 days of incubation, whereas the mass of PEEA coatings dropped up to 80% over the same period (FIG. 2).

EXAMPLE 6

Assessment of Mass Loss of Hydrophobic PEA in PBS and Serum

Figure 3:
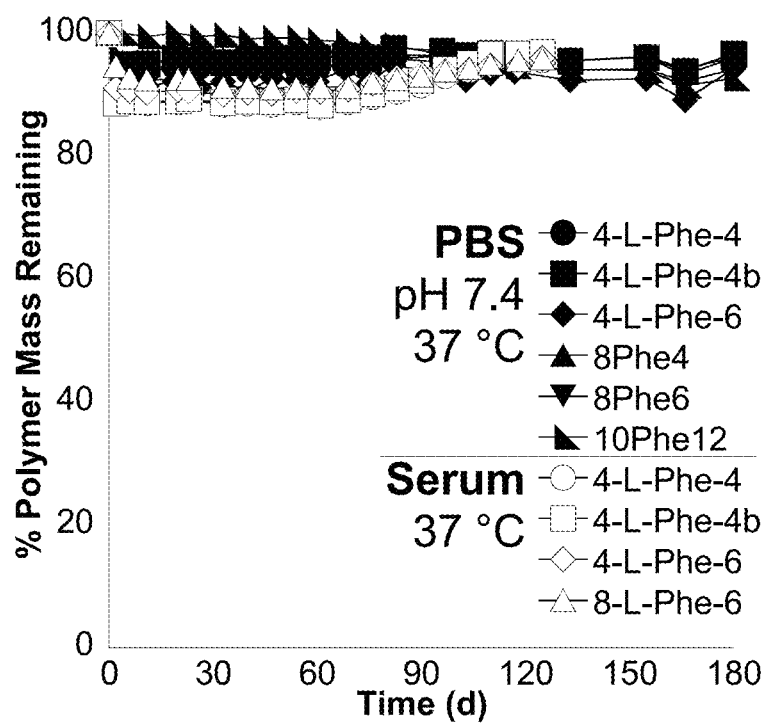
FIG. 3 is a graph of mass loss of PEA coatings on parylene-treated stainless steel stents in PBS, pH 7.4, and in serum at 37° C.

Films, ~1 cm×0.5 mm, of PEAs were prepared by casting from a chloroform solution and evaporating the solution to dryness. Films were placed in 2 mL PBS or horse serum and incubated at 37° C. Degradation was assessed by removing samples, rinsing with water, drying, and weighing. PBS and serum were refreshed at each measurement. None of the PEA films showed significant mass loss over the 180 days in PBS or serum (FIG. 3)

EXAMPLE 7

Assessment of Mass Loss and Appearance of PEEA Coatings In Vivo

In vivo degradation of PEEA coated implants was assessed in a subcutaneous rabbit model. The study was designed to assess degradation over a 12-month period, with endpoints at 1, 3, 6, and 12 months. Numbered, stainless steel rods were weighed and coated as described in Example 4, sterilized by EtO, and implanted subcutaneously in New Zealand white rabbits. Rods were placed a minimum of 1 cm apart along the back of the animal. At the designated end points, the animal was euthanized and the implanted devices were collected. The rod was removed from the surrounding tissue and placed in a separate, labeled vial for residual polymer characterization. Surrounding tissue was collected and placed in a separate, labeled vial. The surrounding tissue was stored at −80° C.

Following explant, the PEEA coating polymer was assessed by several physical and chemical methods:

1) Sample appearance. Tissue was removed from each sample after explant. Samples were disinfected with 10% bleach, rinsed, and dried before imaging. The PEEA coating thinned, turned more opaque, and became patchy over 12 months of implant (FIG. 4).

Figure 5:
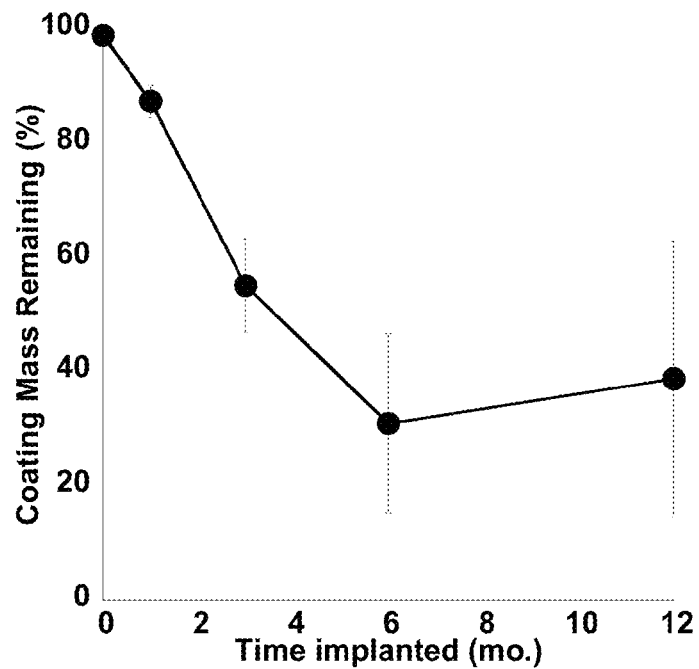
FIG. 5 is a graph showing coating mass of 4-Phe-TEG-8 coatings during in vivo degradation.

2) Mass loss. Samples were dried under vacuum overnight before weighing. The mass of PEEA coating dropped by ~60% over 12 months of implant (FIG. 5).

Figure 6:
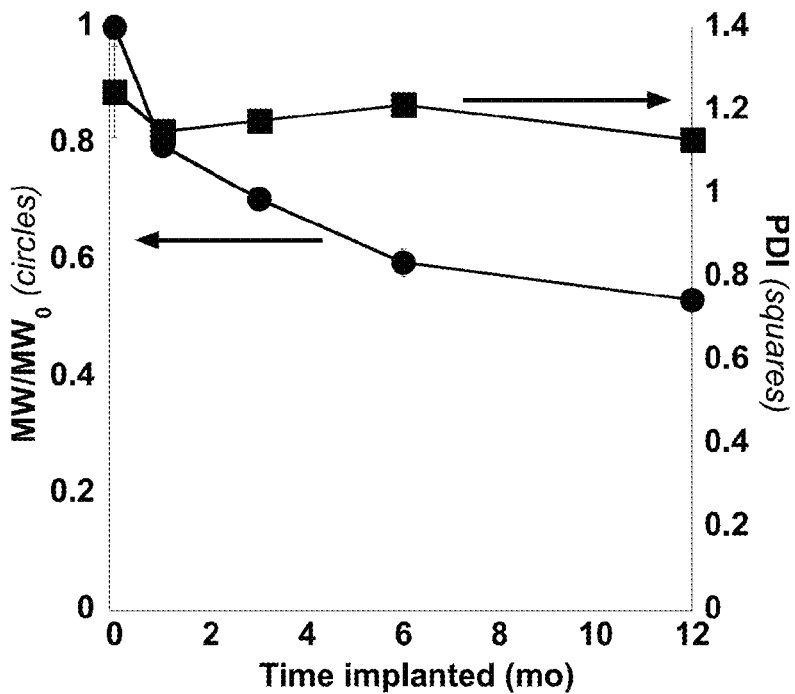
FIG. 6 is molecular weight (circles) and polydispersity (squares) of 4-Phe-TEG-8 polymers after 1, 3, 6, and 12 months of implantation in a subcutaneous model.

3) Molecular weight. Coatings were dissolved in 50 mM NaTFA in THF. Molecular weight was determined by gel permeation chromatography. The molecular weight of the PEEA polymer remaining in the coating decreased by ~50% over 12 months of implant (FIG. 6). The polydispersity of the PEEA polymer remaining in the coating did not change much over the same period.

4) FTIR analysis. FTIR spectra of coatings were obtained with an ATR objective on an infrared microscope. Spectra were obtained directly on coated parts. Analysis of the peak intensities showed that bands associated with hydroxyl and acid moieties increased and bands associated with ester linkages decreased over 12 months of implant (FIG. 7a). This suggests supports the hydrolysis of the PEEA backbone as shown schematically in FIG. 7b.

5) NMR analysis. Coatings were dissolved in deuterated chloroform for NMR. Peak assignment permitted tracking changes in composition of the coating over time (FIG. 8). Peaks associated with the glycol-containing monomer (#3, 4, 5; e.g., monomer (a) (Formula II)) decreased over time whereas those associated with the aliphatic monomer (#1, 2; e.g., monomer (c) (Formula IV)) slightly increased. This suggests degradation removes the more hydrophilic components of the PEEA and points to a source of the difference between PEEA and PEA behavior (that is, degradation of PEEA but not of PEA).

EXAMPLE 8

Assessment of Changes in Appearance of PEA Coatings In Vivo

Figure 10B:
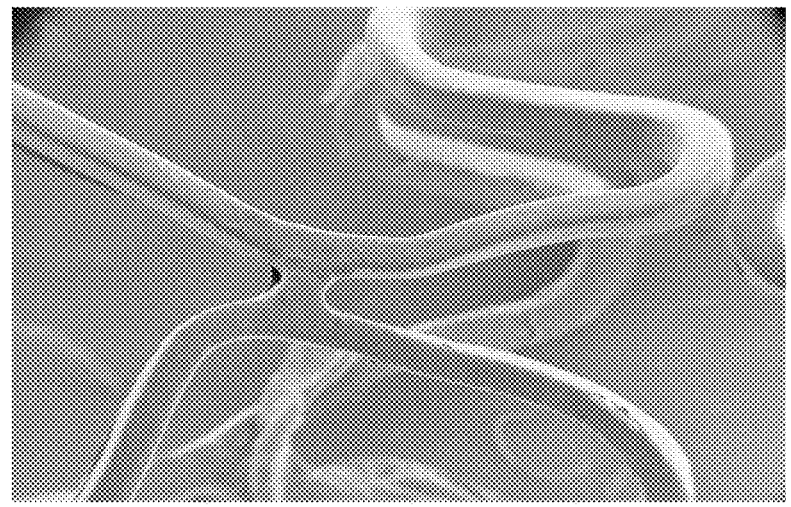

In vivo degradation of PEA coated stents was assessed in a healthy porcine internal mammary artery model. The study was designed to assess degradation over a 3-month period. Stainless steel stents were coated with a 9:1 mixture of the PEAs 8-Phe-6 and 8-Leu-6 as described in Example 4, mounted on balloon catheters, packaged, and sterilized by EtO. Stents were deployed in appropriately-sized coronary arteries. After three months, the animal was sacrificed and arteries containing stents for degradation analysis were dissected without fixation and rinsed with PBS. The arterial bed was dissected, the stent removed, and the neointimal tissue was removed from the stent with a scalpel, forceps, and wooden mandrel. After tissue was removed, the coated stents were disinfected with 10% bleach, which was shown in separate experiments to have no significant effect on coating appearance. The coated area was determined by examining explanted stents with scanning electron microscopy (SEM). The appearance of stents after 90 days in vivo showed nearly complete coatings with little evidence of changes or degradation when compared to t=0 samples (FIG. 10).

What is claimed is:

1. A bioerodable polymeric matrix comprising a bioerodable polymer comprising units of:

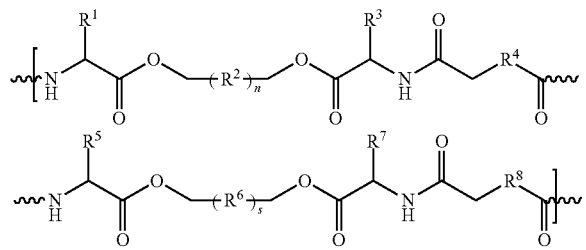

wherein $R^1$, $R^3$, $R^5$, and $R^7$ are independently selected from: —CH(CH$_3$)$_2$, —CH$_2$CH(CH$_3$)$_2$, —CH(CH$_3$)CH$_2$CH$_3$, —(CH$_2$)$_3$CH$_3$, —CH$_2$C$_6$H$_5$, —(CH$_2$)$_2$SCH$_3$, —CH$_3$, —CH$_2$SH, —CH$_2$CO$_2$H, —(CH$_2$)$_2$CO$_2$H, —H, —CH$_2$—imidazole, —(CH$_2$)$_4$NH$_2$, —CH$_2$CONH$_2$, —(CH$_3$)$_3$—N$_a$ (cyclic), —(CH$_2$)$_2$CONH$_2$, —(CH$_2$)$_3$NHC(NH$_2$)$_2^+$, —CH$_2$OH, —CH(CH$_3$)OH, —CH$_2$—indole, and —CH$_2$—C$_6$H$_4$—OH;

$R^2$ and $R^6$ are independently selected from divalent alkane, alkene (hydrocarbylene), and alkoxy (oxyalkylene), wherein the alkoxy is selected from —CH$_2$OCH$_2$—and —CH$_2$OCH$_2$CH$_2$—, wherein $(R^2)_n$ is different than and has a higher hydrophilic-lipophilic ratio than $(R^6)_s$; n is 1 or greater; s is 1 or greater; and $R^4$ and $R^8$ are independently selected from divalent, linear or branched, saturated or unsaturated, C1-C12 fragments wherein at least 50% (w/v) of the bioerodable polymeric matrix is capable of either (a) eroding within 6 months following providing the matrix in a subject wherein the internal environment of said subject causes eroding of the matrix, or (b) eroding within 120 days of incubation of the matrix in phosphate buffered-saline at 37° C., wherein the matrix optionally comprises a bioactive agent.

2. The bioerodable polymeric matrix of claim 1 wherein $R^1$, $R^3$, $R^5$, and $R^7$ are the same.

3. The bioerodable polymeric matrix of claim 1 wherein one or more of $R^1$, $R^3$, $R^5$, and $R^7$ is —CH$_2$C$_6$H$_5$.

4. The bioerodable polymeric matrix of claim 1 wherein $R^2$ is —CH$_2$OCH$_2$—.

5. The bioerodable polymeric matrix of claim 1 wherein n is in the range of 2 to 150.

6. The bioerodable polymeric matrix of claim 1 wherein $R^6$ is a divalent, linear or branched, saturated or unsaturated, C1-C12 fragment.

7. The bioerodable polymeric matrix of claim 6 wherein $R^6$ is —(CH$_2$)—; and s is 6.

8. The bioerodable polymeric matrix of claim 1 wherein the bioerodable polymer of is formed from a composition comprising at least the following monomers:

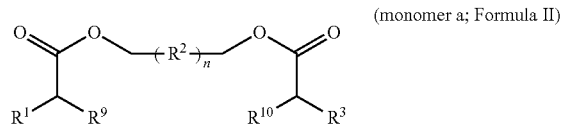

(monomer a; Formula II)

where $R^1$ and $R^3$ are independently selected from: —CH(CH$_3$)$_2$, —CH$_2$CH(CH$_3$)$_2$, —CH(CH$_3$)CH$_2$CH$_3$, —(CH$_2$)$_3$CH$_3$, —CH$_2$C$_6$H$_5$, —(CH$_2$)$_2$SCH$_3$, —CH$_3$, —CH$_2$SH, —CH$_2$CO$_2$H, —(CH$_2$)$_2$CO$_2$H, —H, —CH$_2$—imidazole, —(CH$_2$)$_4$NH$_2$, —CH$_2$CONH$_2$, —(CH$_3$)$_3$—N$_a$ (cyclic), —(CH$_2$)$_2$CONH$_2$, —(CH$_2$)$_3$NHC(NH$_2$)$_2^+$, —CH$_2$OH, —CH(CH$_3$)OH, —CH$_2$—indole, and —CH$_2$—C$_6$H$_4$—OH; $R^2$ is independently selected from divalent alkane, alkene (hydrocarbylene), and alkoxy (oxyalkylene), wherein the alkoxy is selected from —CH$_2$OCH$_2$—and —CH$_2$OCH$_2$CH$_2$—; and n is 1 or greater; and $R^9$ and $R^{10}$ are independently selected from: —NH$_2$ and —NH$_3^+$X$^-$, wherein X is a monovalent atomic or molecular cation;

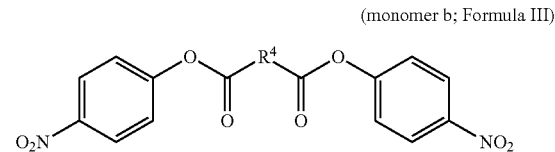

(monomer b; Formula III)

where $R^4$ is divalent, linear or branched, saturated or unsaturated, C1-C12 fragment; and

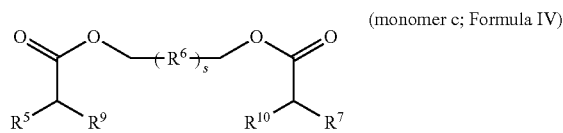

(monomer c; Formula IV)

where $R^5$ and $R^7$ are independently selected from: —CH(CH$_3$)$_2$, —CH$_2$CH(CH$_3$)$_2$, —CH(CH$_3$)CH$_2$CH$_3$, —(CH$_2$)$_3$CH$_3$, —CH$_2$C$_6$H$_5$, —(CH$_2$)$_2$SCH$_3$, —CH$_3$, —CH$_2$SH, —CH$_2$CO$_2$H, —(CH$_2$)$_2$CO$_2$H, —H, —CH$_2$—imidazole, —(CH$_2$)$_4$NH$_2$, —CH$_2$CONH$_2$, —(CH$_3$)$_3$—N$_a$ (cyclic), —(CH$_2$)$_2$CONH$_2$, —(CH$_2$)$_3$NHC(NH$_2$)$_2^+$, —CH$_2$OH, —CH(CH$_3$)OH, —CH$_2$—indole, and —CH$_2$—C$_6$H$_4$—OH; $R^6$ is selected from divalent alkane, alkene (hydrocarbylene), and alkoxy(oxyalkylene), wherein the alkoxy is selected from —CH$_2$OCH$_2$—and —CH$_2$OCH$_2$CH$_2$—; s is 1 or greater; and $R^9$ and $R^{10}$ are independently selected from: —NH$_2$ and —NH$_3^+$X$^-$, wherein X is a monovalent atomic or molecular cation; and where, in the composition, $(R^2)$, of monomer (a) has a higher hydrophilic-lipophilic ratio than $(R^6)_s$, of monomer (c).

9. An implantable or injectable biomedical article, the article comprising the bioerodable polymeric matrix of claim 1 and a bioactive agent.

10. The implantable or injectable biomedical article of claim 9, wherein the polymeric matrix is in the form of a coating.

11. The implantable or injectable biomedical article of claim 10, wherein the coating is present on an intraluminal stent.

12. The implantable or injectable biomedical article of claim 10, wherein 50% (w/v) of the bioerodable polymeric matrix is capable of eroding within 6 months in vivo following implantation in a subject.

13. The implantable or injectable biomedical article of claim 9, wherein the bioerodable polymeric matrix is in the form of a hydrogel.

14. A method for delivering a bioactive agent to a subject comprising implanting the implantable or injectable biomedical article of claim 13 into a subject and allowing the bioactive agent to be released from the bioerodable polymeric matrix.

15. The bioerodable polymeric matrix of claim 5 wherein n is in the range of 2-6.

16. The bioerodable polymeric matrix of claim 1 wherein $R^4$ and $R^8$ are independently selected from the group consisting of: $-CH_2-$, $-(CH_2)_2-$, $-(CH_2)_3-$, $-(CH_2)_4-$, $-(CH_2)_5-$, $-(CH_2)_6-$, $-(CH_2)_7-$, $-(CH_2)_8-$, $-(CH_2)_9-$, $-(CH_2)_{10}-$, $-(CH_2)_{11}-$, and $-(CH_2)_{12}-$.

17. The bioerodable polymeric matrix of claim 1 wherein $R^2$ is $-CH_2OCH_2-$, n is in the range of 2 to 25, and $(R^6)_s$, is a divalent, linear or branched, saturated or unsaturated, C1-C8 fragment.

18. The bioerodable polymeric matrix of claim 17 wherein $R^2$ is $-CH_2OCH_2-$, n is in the range of 2 to 6, and $(R^6)_s$, is a divalent, linear or branched, saturated or unsaturated, C1-C8 fragment.

* * * * *